(12) United States Patent
Celis

(10) Patent No.: US 8,822,182 B2
(45) Date of Patent: *Sep. 2, 2014

(54) CHIMERIC ANTIGEN-SPECIFIC T CELL-ACTIVATING POLYPEPTIDES

(75) Inventor: Esteban Celis, Tampa, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 953 days.

This patent is subject to a terminal disclaimer.

(21) Appl. No.: 12/909,405

(22) Filed: Oct. 21, 2010

(65) Prior Publication Data

US 2011/0071273 A1    Mar. 24, 2011

Related U.S. Application Data

(63) Continuation of application No. 10/478,179, filed as application No. PCT/US02/15992 on May 20, 2002, now Pat. No. 7,842,480.

(60) Provisional application No. 60/291,874, filed on May 18, 2001.

(51) Int. Cl.
*A61K 38/17* (2006.01)
*A61K 38/02* (2006.01)
*C07K 14/47* (2006.01)
*C07K 2/00* (2006.01)

(52) U.S. Cl.
USPC ...... 435/69.7; 530/300; 514/21.3; 424/184.1; 424/185.1; 424/192.1

(58) Field of Classification Search
None
See application file for complete search history.

(56) References Cited

U.S. PATENT DOCUMENTS

| | | | |
|---|---|---|---|
| 4,867,973 A | 9/1989 | Goers et al. | |
| 5,662,907 A | 9/1997 | Kubo et al. | |
| 5,846,827 A | 12/1998 | Celis et al. | |
| 5,965,535 A | 10/1999 | Chaux et al. | |
| 6,037,135 A | 3/2000 | Kubo et al. | |
| 6,210,886 B1 | 4/2001 | Van Baren et al. | |
| 6,419,931 B1 | 7/2002 | Vitiello et al. | |
| 6,534,482 B1 | 3/2003 | Fikes et al. | |
| 6,602,510 B1 | 8/2003 | Fikes et al. | |
| 6,602,705 B1* | 8/2003 | Barnett et al. | 435/320.1 |
| 6,686,147 B1 | 2/2004 | Scanlan et al. | |
| 6,689,363 B1 | 2/2004 | Sette et al. | |
| 6,794,501 B2 | 9/2004 | Chen et al. | |
| 7,026,443 B1 | 4/2006 | Sette et al. | |
| 7,049,413 B2 | 5/2006 | Zhang et al. | |
| 7,252,829 B1 | 8/2007 | Sette et al. | |
| 7,348,177 B2 | 3/2008 | Lian et al. | |
| 7,611,713 B2 | 11/2009 | Sette et al. | |
| 7,842,480 B2 | 11/2010 | Celis | |
| 7,851,212 B2* | 12/2010 | Berinstein et al. | 435/320.1 |
| 8,263,560 B2 | 9/2012 | Strome et al. | |
| 2004/0053822 A1 | 3/2004 | Fikes et al. | |
| 2004/0054137 A1 | 3/2004 | Thomson et al. | |
| 2004/0249126 A1 | 12/2004 | Celis | |
| 2005/0196403 A1 | 9/2005 | Fikes et al. | |
| 2005/0271676 A1 | 12/2005 | Sette et al. | |
| 2006/0057115 A1 | 3/2006 | zur Megede et al. | |
| 2006/0222656 A1 | 10/2006 | Strome et al. | |
| 2007/0014810 A1 | 1/2007 | Baker et al. | |
| 2007/0020327 A1 | 1/2007 | Fikes et al. | |
| 2007/0031424 A1 | 2/2007 | Muyldermans | |
| 2007/0053922 A1 | 3/2007 | Sette et al. | |
| 2007/0055049 A1 | 3/2007 | Grey et al. | |
| 2007/0059799 A1 | 3/2007 | Sette et al. | |
| 2007/0098776 A1 | 5/2007 | Fikes et al. | |
| 2008/0044407 A1 | 2/2008 | Strome et al. | |
| 2010/0183646 A1 | 7/2010 | Strome et al. | |
| 2011/0070252 A1 | 3/2011 | Strome et al. | |

FOREIGN PATENT DOCUMENTS

| | | | |
|---|---|---|---|
| WO | WO-97/33602 | 9/1997 | |
| WO | WO-99/45954 | 9/1999 | |
| WO | WO-99/61916 | 12/1999 | |
| WO | WO 00/34308 | * 6/2000 | |
| WO | WO-00/52045 | 9/2000 | |
| WO | WO-01/42267 | 6/2001 | |
| WO | WO-01/90197 | 11/2001 | |
| WO | WO-03/000907 | 1/2003 | |
| WO | WO-03/040165 | 5/2003 | |
| WO | WO-2005/037190 | 4/2005 | |
| WO | WO-2005/089164 | 9/2005 | |
| WO | WO-2006/091734 | 8/2006 | |
| WO | WO-2006/106435 | 10/2006 | |
| WO | WO-2006/113622 | 10/2006 | |

OTHER PUBLICATIONS

Haas et al., Eur. J. Immunol., 1991, vol. 21:1371-1377.*
Diez-Rivero et al., PLoS One, 2012, vol. 7(8)1 -8.*
U.S. Appl. No. 09/350,401, Jul. 8, 1999, Sette.
Lu, et al. (2004) "Mulitepitope Trojan Antigen Peptide Vaccines for the Induction of Antitumor CTL and Th Immune Responses," J. Immunol. 172:4575-4582.
Van Der Bruggen, et al. (2002) "Tumor-Specific Antigenic Peptides Recognized by Human T Cells," Immunological Reviews, 188(1):51-64.
Tang, et al. (1999) "The Carbosyl Terminus of RNA Helicase A Contains a Bidirectional Nuclear Transport Domain," Mol. Cell Biol., 19(5):3540-3550.

(Continued)

*Primary Examiner* — Xiaozhen Xie

(74) *Attorney, Agent, or Firm* — Cooley LLP

(57) ABSTRACT

The invention provides an immunogenic or antigenic polypeptide containing a translocation domain, a peptide epitope, at least one biologically active agent, and cleavage sites. These polypeptides are useful for activating T cell responses.

7 Claims, 13 Drawing Sheets

(56) References Cited

OTHER PUBLICATIONS

Gil-Torregrosa, et al. (1998) "Major Histocompatability Complex Class I Viral Antigen Processing in the Secretory Pathway Defined by the trans-Golgi Netweork Protease Furin," J. Exp. Med. 188(6):1105-1116.

Kim et al. (1997) "Introduction of Soluble Proteins into the MHC Class I Pathway by Conjugation to an HIV tat Peptide," J. Immunol. 159:1666-1668.

Ishioka, et al. (1999) "Utilization of MHC Class I Transgeneic Mice for Development of Minigene DNA Vaccines Encoding Multiple HLA-Restricted CTL Epitopes," J. Immunol., 162:3915-3925.

Lees et al. (2000) "The Effect of T1 and T2 Cytokines on the Cytotoxic T cell Resposne to Mannan-MUC1" Cancer Immunol. Immunotther. 48(11):644-652 (Abstract Only).

Heuser et al. (2003) "Anti-MUC1-Antibody-Interleukin-2 Fusion Protein that Activates Resting NK Cells t Lysis of MUC1-Positive Tumour Cells," Br. J. Cancer, 89:1130-1139.

Baldwin, et al. (2003) Vaccinia-Expressed Human Papillomavirus 16 and 18 E6 and E7 as Therapeutic Vaccination for Vulvul and Vaginal Intraepithelial Neoplasia, Clin. Cancer Res., 9:5205-5213.

Van Der Burg, et al. (2001) "Natural T-Helper Immunity Against Human Papillomavirus Type 16 (HPV16) E7-Derived Peptide Epitopes in Pateints with HPV16-Positive Cervical Cancer Lesions: Identification of 3 Human Leukocyte Antigen Class II-Restricted Epitopes," Int. J. Cancer, 91:612-618.

BioAfrica, "HIV-1 Protease Cleavage Sites," 4 pages, http://www.bioafrica.net/proteomics/HIVcleavagesites.html (accessed Aug. 29, 2013).

Chomez et al., "An Overview of the MAGE Gene Family with the Identification of All Human Members of the Family," Canc. Res. 61:5544-5551 (2001).

Final Rejection mailed Mar. 30, 2009 in Co-Pending U.S. Appl. No. 11/391,632.

Preliminary Amendment filed Apr. 7, 2010 in Co-Pending U.S. Appl. No. 12/696,385.

Wang et al., "A Systematic Assessment of MHC Class II Peptide Binding Predictions and Evaluation of a Consensus Approach," PLoS Comput. Biol. 4:e1000048, 10 pages (2008).

\* cited by examiner

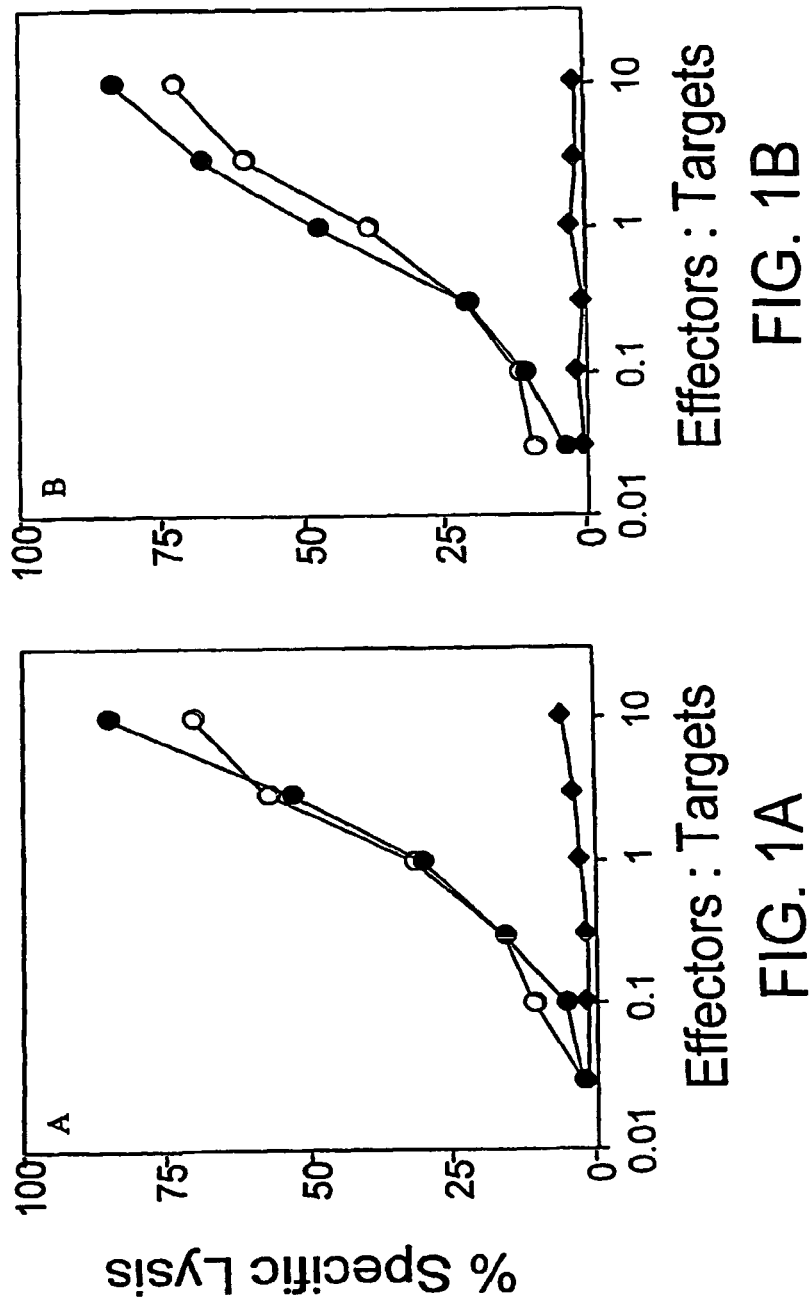

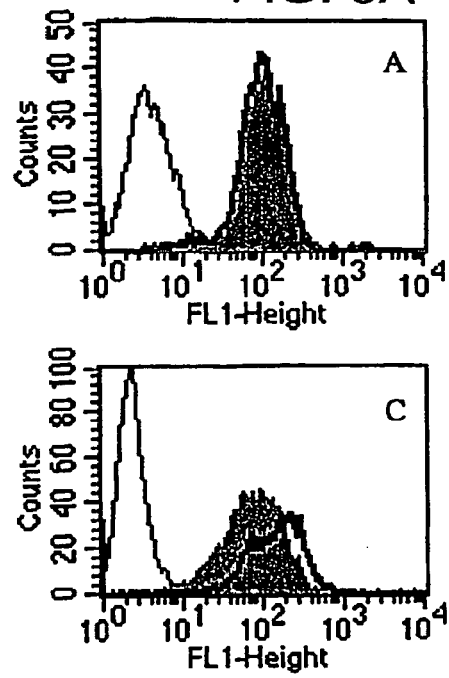
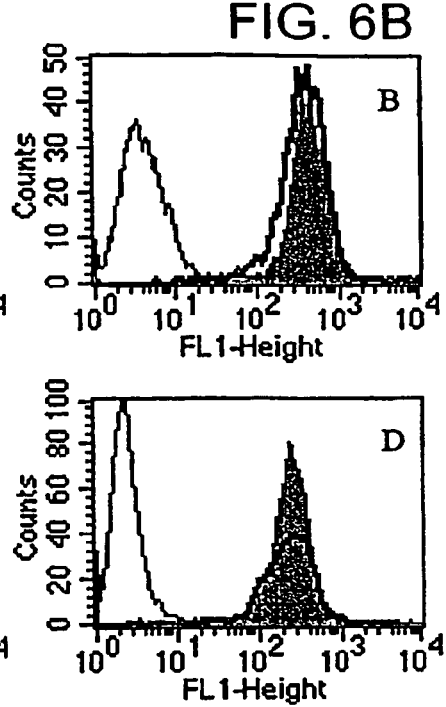
FIG. 6A
FIG. 6B
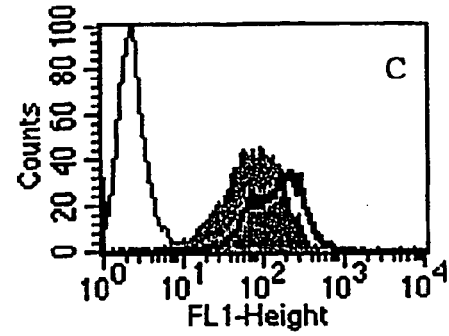
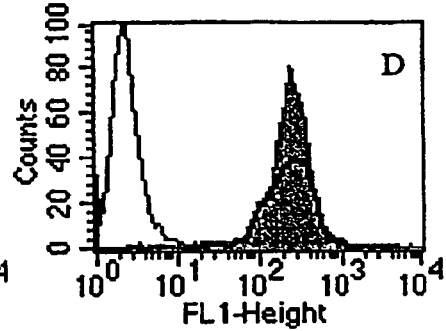
FIG. 6C
FIG. 6D
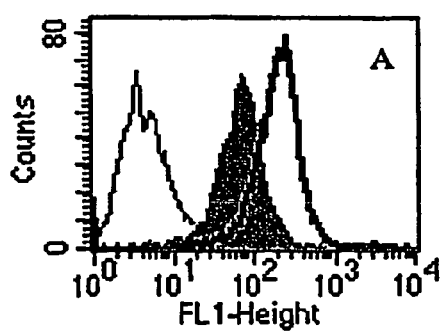
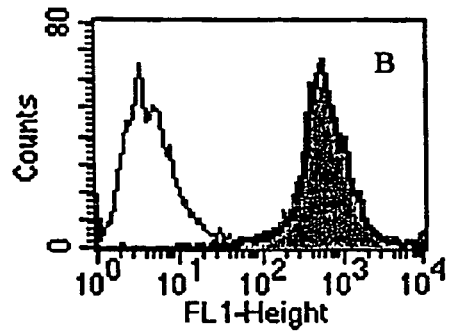
FIG. 7A
FIG. 7B
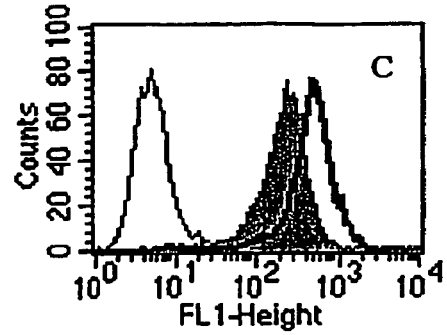
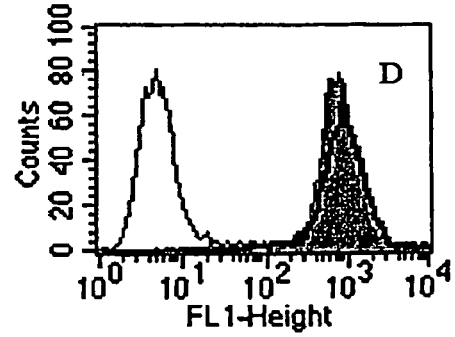
FIG. 7C
FIG. 7D

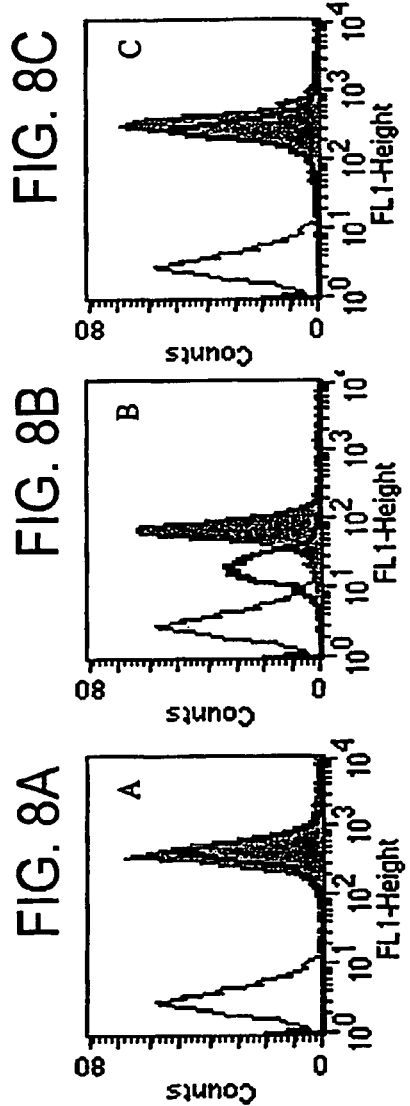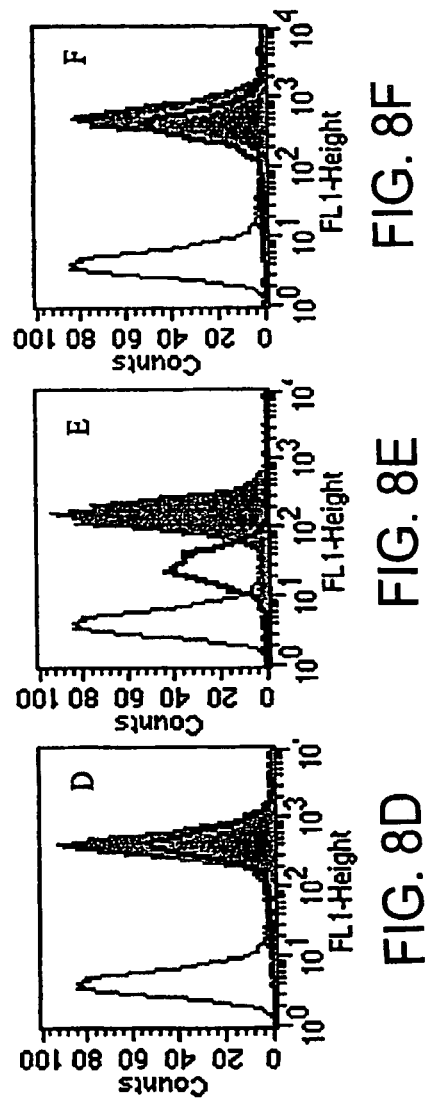

SEQUENCE LISTING

```
<160> NUMBER OF SEQ ID NOS: 38

<210> SEQ ID NO 1
<211> LENGTH: 9
<212> TYPE: PRT
<213> ORGANISM: HIV

<400> SEQUENCE: 1

Arg Lys Lys Arg Arg Gln Arg Arg Arg
1               5

<210> SEQ ID NO 2
<211> LENGTH: 16
<212> TYPE: PRT
<213> ORGANISM: Drosophila melanogaster

<400> SEQUENCE: 2

Arg Gln Ile Lys Ile Trp Phe Pro Asn Arg Arg Met Lys Trp Lys Lys
1               5                   10                  15

<210> SEQ ID NO 3
<211> LENGTH: 25
<212> TYPE: PRT
<213> ORGANISM: Homo sapiens

<400> SEQUENCE: 3

Met Ala Ile Ser Gly Val Pro Val Leu Gly Phe Phe Ile Ile Ala Val
1               5                   10                  15

Leu Met Ser Ala Gln Glu Ser Trp Ala
            20                  25

<210> SEQ ID NO 4
<211> LENGTH: 4
<212> TYPE: PRT
<213> ORGANISM: Rattus norvegicus

<400> SEQUENCE: 4

Lys Asp Glu Leu
1

<210> SEQ ID NO 5
<211> LENGTH: 5
<212> TYPE: PRT
<213> ORGANISM: Bos taurus

<400> SEQUENCE: 5

Lys Phe Glu Arg Gln
1               5

<210> SEQ ID NO 6
```

```
<211> LENGTH: 15
<212> TYPE: PRT
<213> ORGANISM: Homo sapiens

<400> SEQUENCE: 6

Met Asp Asp Gln Arg Asp Leu Ile Ser Asn Asn Glu Gln Leu Pro
1               5                   10                  15

<210> SEQ ID NO 7
<211> LENGTH: 4
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = Lys or Arg

<400> SEQUENCE: 7

Arg Xaa Xaa Arg
1

<210> SEQ ID NO 8
<211> LENGTH: 4
<212> TYPE: PRT
<213> ORGANISM: Artificial Sequence
<220> FEATURE:
<223> OTHER INFORMATION: linker peptide

<400> SEQUENCE: 8

Arg Val Lys Arg
1

<210> SEQ ID NO 9
<211> LENGTH: 4
<212> TYPE: PRT
<213> ORGANISM: Artificial Sequence
<220> FEATURE:
<223> OTHER INFORMATION: linker peptide

<400> SEQUENCE: 9

Val Arg Val Val
1

<210> SEQ ID NO 10
<211> LENGTH: 9
<212> TYPE: PRT
<213> ORGANISM: Artificial Sequence
<220> FEATURE:
<223> OTHER INFORMATION: epitope

<400> SEQUENCE: 10

Ile Met Asp Gln Val Pro Phe Ser Val
1               5

<210> SEQ ID NO 11
<211> LENGTH: 5
<212> TYPE: PRT
<213> ORGANISM: Influenza A virus

<400> SEQUENCE: 11

Ala Glu Ile Asp Leu
1               5
```

<210> SEQ ID NO 12
<211> LENGTH: 5
<212> TYPE: PRT
<213> ORGANISM: Influenza A virus

<400> SEQUENCE: 12

Leu Arg Thr Glu Asp
 1               5

<210> SEQ ID NO 13
<211> LENGTH: 35
<212> TYPE: PRT
<213> ORGANISM: Artificial Sequence
<220> FEATURE:
<223> OTHER INFORMATION: synthetic peptide

<400> SEQUENCE: 13

Arg Gln Ile Lys Ile Trp Phe Pro Asn Arg Arg Met Lys Trp Lys Lys
 1               5                  10                  15

Ala Glu Ile Asp Leu Ile Met Asp Gln Val Pro Phe Ser Val Leu Arg
            20                  25                  30

Thr Glu Asp
        35

<210> SEQ ID NO 14
<211> LENGTH: 78
<212> TYPE: DNA
<213> ORGANISM: Artificial Sequence
<220> FEATURE:
<223> OTHER INFORMATION: primer

<400> SEQUENCE: 14
gacgacgaca agatgcgtca gatcaagatc tggttcccga accgtcgtat gaagtggaag      60
aaggcagaga tcgacctg                                                   78

<210> SEQ ID NO 15
<211> LENGTH: 76
<212> TYPE: DNA
<213> ORGANISM: Artificial Sequence
<220> FEATURE:
<223> OTHER INFORMATION: primer

<400> SEQUENCE: 15
gaggagaagc ccggtctagt cttcggtacg cagtacagag aacggtacct ggtccatgat      60
caggtcgatc tctgcc                                                     76

<210> SEQ ID NO 16
<211> LENGTH: 9
<212> TYPE: PRT
<213> ORGANISM: Artificial Sequence
<220> FEATURE:
<223> OTHER INFORMATION: epitope

<400> SEQUENCE: 16

Ile Met Ile Gly Val Leu Val Gly Val
 1               5

<210> SEQ ID NO 17
<211> LENGTH: 21
<212> TYPE: PRT
<213> ORGANISM: Artificial Sequence
<220> FEATURE:
<223> OTHER INFORMATION: synthetic peptide

```
<400> SEQUENCE: 17

Ile Met Ile Gly Val Leu Val Gly Val Ala Ala Ala Arg Lys Lys Arg
1               5                   10                  15

Arg Gln Arg Arg Arg
            20

<210> SEQ ID NO 18
<211> LENGTH: 10
<212> TYPE: PRT
<213> ORGANISM: Artificial Sequence
<220> FEATURE:
<223> OTHER INFORMATION: epitope

<400> SEQUENCE: 18

Phe Leu Pro Ser Asp Tyr Phe Pro Ser Val
1               5                   10

<210> SEQ ID NO 19
<211> LENGTH: 13
<212> TYPE: PRT
<213> ORGANISM: Artificial Sequence
<220> FEATURE:
<223> OTHER INFORMATION: synthetic peptide

<400> SEQUENCE: 19

Ile Met Ile Gly Val Leu Val Gly Val Ala Ala Ala Arg
1               5                   10

<210> SEQ ID NO 20
<211> LENGTH: 12
<212> TYPE: PRT
<213> ORGANISM: Artificial Sequence
<220> FEATURE:
<223> OTHER INFORMATION: synthetic peptide

<400> SEQUENCE: 20

Ile Met Ile Gly Val Leu Val Gly Val Lys Lys Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: synthetic peptide

<400> SEQUENCE: 21

Ile Met Ile Gly Val Leu Val Gly Val Arg Arg Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: synthetic peptide

<400> SEQUENCE: 22

Ile Met Ile Gly Val Leu Val Gly Val Arg Lys Lys
1               5                   10

<210> SEQ ID NO 23
<211> LENGTH: 21
<212> TYPE: PRT
<213> ORGANISM: Artificial Sequence
```

```
<220> FEATURE:
<223> OTHER INFORMATION: synthetic peptide

<400> SEQUENCE: 23

Arg Lys Lys Arg Arg Gln Arg Arg Arg Ala Ala Ala Ile Met Ile Gly
 1               5                  10                  15

Val Leu Val Gly Val
            20

<210> SEQ ID NO 24
<211> LENGTH: 20
<212> TYPE: PRT
<213> ORGANISM: Artificial Sequence
<220> FEATURE:
<223> OTHER INFORMATION: synthetic peptide

<400> SEQUENCE: 24

Ser Ile Ile Asn Phe Glu Lys Leu Ala Ala Ala Arg Lys Lys Arg Arg
 1               5                  10                  15

Gln Arg Arg Arg
            20

<210> SEQ ID NO 25
<211> LENGTH: 20
<212> TYPE: PRT
<213> ORGANISM: Artificial Sequence
<220> FEATURE:
<223> OTHER INFORMATION: synthetic peptide

<400> SEQUENCE: 25

Arg Lys Lys Arg Arg Gln Arg Arg Arg Ala Ala Ala Ser Ile Ile Asn
 1               5                  10                  15

Phe Glu Lys Leu
            20

<210> SEQ ID NO 26
<211> LENGTH: 13
<212> TYPE: PRT
<213> ORGANISM: Artificial Sequence
<220> FEATURE:
<223> OTHER INFORMATION: synthetic peptide

<400> SEQUENCE: 26

Ser Ile Ile Asn Phe Glu Lys Leu Ala Ala Ala Arg Lys
 1               5                  10

<210> SEQ ID NO 27
<211> LENGTH: 8
<212> TYPE: PRT
<213> ORGANISM: Artificial Sequence
<220> FEATURE:
<223> OTHER INFORMATION: epitope

<400> SEQUENCE: 27

Ser Ile Tyr Arg Tyr Tyr Gly Leu
 1               5

<210> SEQ ID NO 28
<211> LENGTH: 47
<212> TYPE: PRT
<213> ORGANISM: Artificial Sequence
<220> FEATURE:
<223> OTHER INFORMATION: synthetic peptide

<400> SEQUENCE: 28
```

-continued

```
Ile Lys Ala Val Tyr Asn Phe Ala Thr Cys Gly Arg Val Lys Arg Ser
1               5                   10                  15

Ile Tyr Arg Tyr Tyr Gly Leu Arg Val Lys Arg Ser Ile Ile Asn Phe
                20                  25                  30

Glu Lys Leu Ala Ala Ala Arg Lys Lys Arg Arg Gln Arg Arg
            35                  40                  45
```

<210> SEQ ID NO 29
<211> LENGTH: 47
<212> TYPE: PRT
<213> ORGANISM: Artificial Sequence
<220> FEATURE:
<223> OTHER INFORMATION: synthetic peptide

<400> SEQUENCE: 29

```
Ile Lys Ala Val Tyr Asn Phe Ala Thr Cys Gly Val Arg Val Val Ser
1               5                   10                  15

Ile Tyr Arg Tyr Tyr Gly Leu Val Arg Val Val Ser Ile Ile Asn Phe
                20                  25                  30

Glu Lys Leu Ala Ala Ala Arg Lys Lys Arg Arg Gln Arg Arg
            35                  40                  45
```

<210> SEQ ID NO 30
<211> LENGTH: 47
<212> TYPE: PRT
<213> ORGANISM: Artificial Sequence
<220> FEATURE:
<223> OTHER INFORMATION: synthetic peptide

<400> SEQUENCE: 30

```
Ser Ile Ile Asn Phe Glu Lys Leu Arg Val Lys Arg Ile Lys Ala Val
1               5                   10                  15

Tyr Asn Phe Ala Thr Cys Gly Arg Val Lys Arg Ser Ile Tyr Arg Tyr
                20                  25                  30

Tyr Gly Leu Ala Ala Ala Arg Lys Lys Arg Arg Gln Arg Arg Arg
            35                  40                  45
```

<210> SEQ ID NO 31
<211> LENGTH: 11
<212> TYPE: PRT
<213> ORGANISM: Artificial Sequence
<220> FEATURE:
<223> OTHER INFORMATION: epitope

<400> SEQUENCE: 31

```
Ile Lys Ala Val Tyr Asn Phe Ala Thr Cys Gly
1               5                   10
```

<210> SEQ ID NO 32
<211> LENGTH: 44
<212> TYPE: PRT
<213> ORGANISM: Artificial Sequence
<220> FEATURE:
<223> OTHER INFORMATION: synthetic peptide

<400> SEQUENCE: 32

```
Arg Lys Lys Arg Arg Gln Arg Arg Ile Lys Ala Val Tyr Asn Phe
1               5                   10                  15

Ala Thr Cys Gly Arg Val Lys Arg Ser Ile Ile Asn Phe Glu Lys Leu
                20                  25                  30

Arg Val Lys Arg Ser Ile Tyr Arg Tyr Tyr Gly Leu
            35                  40
```

```
<210> SEQ ID NO 33
<211> LENGTH: 10
<212> TYPE: PRT
<213> ORGANISM: Artificial Sequence
<220> FEATURE:
<223> OTHER INFORMATION: epitope

<400> SEQUENCE: 33

Ser Gly Pro Ser Asn Thr Pro Pro Glu Ile
1               5                   10

<210> SEQ ID NO 34
<211> LENGTH: 9
<212> TYPE: PRT
<213> ORGANISM: Artificial Sequence
<220> FEATURE:
<223> OTHER INFORMATION: epitope

<400> SEQUENCE: 34

Leu Pro Tyr Leu Gly Trp Leu Val Phe
1               5

<210> SEQ ID NO 35
<211> LENGTH: 10
<212> TYPE: PRT
<213> ORGANISM: Artificial Sequence
<220> FEATURE:
<223> OTHER INFORMATION: epitope

<400> SEQUENCE: 35

Ser Val Tyr Asp Glu Phe Phe Val Trp Leu
1               5                   10

<210> SEQ ID NO 36
<211> LENGTH: 49
<212> TYPE: PRT
<213> ORGANISM: Artificial Sequence
<220> FEATURE:
<223> OTHER INFORMATION: synthetic peptide

<400> SEQUENCE: 36

Arg Lys Lys Arg Arg Gln Arg Arg Ala Ala Ala Ser Val Tyr Asp
1               5                   10                  15

Glu Phe Phe Val Trp Leu Lys Val Lys Arg Leu Pro Tyr Leu Gly Trp
            20                  25                  30

Leu Val Phe Lys Val Lys Arg Ser Gly Pro Ser Asn Thr Pro Pro Glu
        35                  40                  45

Ile

<210> SEQ ID NO 37
<211> LENGTH: 49
<212> TYPE: PRT
<213> ORGANISM: Artificial Sequence
<220> FEATURE:
<223> OTHER INFORMATION: synthetic peptide

<400> SEQUENCE: 37

Arg Lys Lys Arg Arg Gln Arg Arg Ala Ala Ala Ser Val Tyr Asp
1               5                   10                  15

Glu Phe Phe Val Trp Leu Val Arg Val Val Leu Pro Tyr Leu Gly Trp
            20                  25                  30

Leu Val Phe Val Arg Val Val Ser Gly Pro Ser Asn Thr Pro Pro Glu
        35                  40                  45
```

Ile

```
<210> SEQ ID NO 38
<211> LENGTH: 8
<212> TYPE: PRT
<213> ORGANISM: Artificial Sequence
<220> FEATURE:
<223> OTHER INFORMATION: epitope

<400> SEQUENCE: 38

Ser Ile Ile Asn Phe Glu Lys Leu
 1               5
```

CHIMERIC ANTIGEN-SPECIFIC T CELL-ACTIVATING POLYPEPTIDES

This application is a continuation of U.S. application Ser. No. 10/478,179 (filed Jun. 16, 2004), now U.S. Pat. No. 7,842,480, which claims priority to International Application PCT/US02/15992 filed May 20, 2002, which claims priority to Provisional Application No. 60/291,874, filed May 18, 2001, which applications are hereby incorporated by reference in their entireties.

This invention was made with government support under CA080782, CA082677, and CA015083 awarded by the National Cancer Institute. The government has certain rights in the invention.

TECHNICAL FIELD

This invention relates to immunogenic molecules and more particularly to immunogenic polypeptides capable of being processed into peptide epitopes recognizable by T lymphocytes, e.g., cytotoxic T lymphocytes.

BACKGROUND

Cytotoxic T lymphocytes (CTL) are important effectors of immunity to pathological conditions such as microbial infections and cancer in that they have the ability to destroy "abnormal" cells such as those infected by intracellular pathogens or tumor cells. CTL recognize these abnormal cells as "foreign" via cell-surface antigen-specific T cell receptors (TCR), which bind to antigenic peptide epitopes complexed with major histocompatibility complex (MHC) molecules (most commonly MHC class I molecules) on the surface of the abnormal cells. CTL peptide epitopes are generally derived from intracellular proteins such as microbial (e.g., viral) proteins and tumor-associated antigens that are: (i) synthesized within the cell; (ii) proteolytically processed within the cell; and (iii) transported by the TAP transporter molecules into the endoplasmic reticulum (ER) [Germain et al. (1994) Cell 76:287; York et al. (1996) Annual Review of Immunology 14:369; Heemels et al. (1995) Annu Rev Biochem 64:463; Momburg et al. (1998) Adv Immunol 68:191]. Once in the ER, the CTL peptide epitopes can be further "trimmed" by the action of peptidases into an optimal size for association with MHC class I molecules; after complexing of CTL peptide epitopes with an appropriate MHC class I molecule, the resulting complex is exported to the cell-surface where it is available for recognition by a relevant TCR [Snyder et al. (1994) J Exp Med 180:2389; Roelse et al. (1994) J Exp Med 180:1591; Mo et al. (1999) J Immunol 163:5851; Paz et al. (1999) Immunity 11:241; Powis et al. (1996) Immunity 4:159; Yewdell et al. (2001) Curr Opin Immunol 13:13]. This process is known as the "MHC class I antigen-processing pathway."

The requirement for intracellular processing of antigens creates some constraints on the ability to induce CTL responses using exogenous, non-infectious vaccines such as killed pathogens or protein antigens. These constraints arise because cells, e.g., antigen presenting cells (APC), are generally not very efficient at processing via the MHC class I antigen-processing pathway antigens that are not synthesized within the cell but are imported into the cell by any of the mechanisms by which such importation occurs.

SUMMARY

The present invention is based on the discovery of immunogenic polypeptides designated herein interchangeably as "fusion agents" or "Trojan Antigens" ("TA") that when provided to mammalian cells have the ability to enter the cell and be processed by the cell into one or more epitopes recognizable by T cells, e.g., CTL, on the surface of the cell. The invention features these fusion agents, nucleic acids encoding the fusion agents, and cells containing the nucleic acids. In addition, the invention provides methods of making a cell immunogenic or antigenic and methods of making the fusion agents of the invention.

More specifically, the invention features a fusion agent comprising: (a) a transport domain; (b) at least two cleavage sites; (c) a peptide epitope recognized by an antigen specific receptor on an effector T lymphocyte or an effector T lymphocyte precursor cell; and (d) at least one biologically active agent; there is a cleavage site between the peptide epitope and the at least one biologically active agent and between each biologically active agent. The effector T lymphocyte can be a cytotoxic T lymphocyte (CTL) and the effector T lymphocyte precursor cell can be a CTL precursor cell. Alternatively, the effector T lymphocyte can be a helper T lymphocyte (HTL) and the effector T lymphocyte precursor cell can be a HTL precursor cell. The peptide epitope can be one that binds to a major histocompatibility complex (MHC) class I molecule or to a MHC class II molecule. There can be a cleavage site between the transport domain and the peptide epitope or between the transport domain and the at least one biologically active agent. The transport domain can contain all or part of a cleavage site. The transport domain can be or contain a HIVtat domain (SEQ ID NO:1), an amino acid sequence consisting of SEQ ID NO:2, an amino acid sequence consisting of SEQ ID NO:3, or a polypeptide consisting of a polyarginine sequence of 7-20 arginine residues. The at least two cleavage sites can be proteolytic enzyme cleavage sites and the proteolytic enzyme can be a member of the furin family of enzymes. The at least one biologically active agent can be: (i) a second peptide epitope recognized by a CTL or a CTL precursor cell or (ii) a peptide epitope recognized by a HTL or a HTL precursor cell. Alternatively, the at least one biologically active agent can be a cytokine or a functional fragment of a cytokine.

The invention also encompasses a nucleic acid comprising a nucleotide sequence that encodes the fusion agent of the invention, a vector (e.g., a vector that includes a transcriptional regulatory element (TRE) operably linked to the nucleotide sequence) containing the nucleic acid, and a cell (e.g., a prokaryotic cell or a eukaryotic cell) containing the vector.

Also embraced by the invention is a method of making a cell immunogenic or antigenic; the method involves delivering the fusion agent of the invention to the inside of the cell. The delivery can be by contacting the cell with the fusion agent or by contacting the cell with a nucleic acid encoding the fusion agent. In addition, the delivery can be in vitro or the cell can be in a mammal. Where the cell is in a mammal, the fusion agent or a nucleic acid encoding the fusion agent can be administered to the mammal. The mammal can have an infectious disease, e.g., a viral disease, a bacterial disease, a protozoan disease, a fungal disease, or a yeast disease. Alternatively, the mammal can have a proliferative cell disease, e.g., a cancer such as a neural tissue cancer, melanoma, breast cancer, lung cancer, a gastrointestinal cancer, ovarian cancer, testicular cancer, lung cancer, prostate cancer, cervical cancer, bladder cancer, vaginal cancer, liver cancer, renal cancer, bone cancer, a hematological cell cancer, or a vascular tissue cancer.

Alternatively, the method can involve: (a) providing a recombinant cell which is the progeny of a cell obtained from the mammal and has been transfected or transformed ex vivo with a nucleic acid encoding fusion agent so that the cell expresses the fusion agent; and (b) administering the recombinant cell or a progeny cell of the recombinant cell to the mammal.

The invention is also embodies a method of making a recombinant cell. This method includes the steps of (a) providing a cell which is a cell obtained from the mammal or is a progeny cell of a cell obtained from the mammal; and (b) making a recombinant cell by transfecting or transforming the cell ex vivo with a nucleic acid encoding the fusion agent, such that the recombinant cell expresses the fusion agent. The recombinant cell or a progeny cell of the recombinant cell can, optionally, then be administered to the mammal.

The invention also provides a method of producing a fusion agent. The method involves culturing a cell of the invention (e.g., a cell containing a vector that includes a transcriptional regulatory element (TRE) operably linked to a nucleotide sequence that encodes the fusion agent); and (b) extracting the fusion agent from the culture.

As used herein, a "transport domain" is a component of a fusion agent of the invention that mediates transport of the fusion agent across biological (e.g., cell surface and/or intracellular) membranes. The transport domains can be naturally occurring or synthetic and will preferably be polypeptide in nature.

As used herein, a "cleavage site" in a fusion agent of the invention is a segment of the fusion agent at which cleavage of the fusion agent into physically separate parts can occur. Cleavage sites can be, for example, proteolytic enzyme recognition amino acid sequences (e.g., furin recognition sequences) or sites at which chemical or photoactivated cleavage can take place.

As used herein, a "biologically active agent" is a component of a fusion agent of the invention that mediates a biological activity. A biologically active agent can be, for example, an additional peptide epitope recognizable by an antigen-specific T cell receptor. Thus, where a fusion agent of the invention contains one biologically active agent that is a peptide epitope, the fusion agent will contain two peptide epitopes and, where a fusion agent of the invention contains two biologically active agents that are both peptide epitopes, the fusion agent will contain three peptide epitopes, etc. Other useful biologically active agents are listed herein.

As used herein, an "effector. T lymphocyte" is a T lymphocyte having immunological activity. Such immunological activity can be, without limitation, cytotoxic activity, helper activity, suppressive activity, immune-deviating activity, inflammatory activity, or pro-inflammatory activity.

As used herein, an "effector T lymphocyte precursor cell" is a T lymphocyte that, subsequent to activation, has any of the above immunological activities. Activation can be, without limitation, by recognition of the relevant peptide epitope-major histocompatibility complex (MHC) molecular complex by a TCR on the effector T lymphocyte precursor cell or by a non-specific stimulus, e.g., a T cell mitogen such as Concanavalin A. Thus, an effector T lymphocyte precursor cell can be a "virgin" T lymphocyte that has never previously been activated or a "memory" T lymphocyte that has previously been activated or the progeny of such a memory T lymphocyte.

As used herein, a "cytotoxic T lymphocyte" ("CTL") is a T lymphocyte that can kill a target cell expressing on its surface a peptide epitope-major histocompatibility complex (MHC) molecular complex for which the TCR of the CTL is specific.

As used herein, a "CTL precursor cell" is a T lymphocyte that can, subsequent to activation, kill a target cell expressing on its surface a peptide epitope-major histocompatibility complex (MHC) molecular complex for which the TCR of the CTL is specific. Activation can be, without limitation, by recognition of the relevant peptide epitope-major histocompatibility complex (MHC) molecular complex by a TCR on the CTL precursor cell or by a non-specific stimulus, e.g., a T cell mitogen such as Concanavalin A. Thus, a CTL precursor cell can be a "virgin" T lymphocyte that has never previously been activated or a "memory" T lymphocyte that has previously been activated or the progeny of such a memory T lymphocyte.

As used herein, a "helper T lymphocyte" ("HTL") is a T lymphocyte that provides helper activity in an immune response. Such an immune response can be, for example, an antibody-producing response of a B lymphocyte, a response of a CTL precursor cell, or an inflammatory or pro-inflammatory response of a variety of leukocyte types.

As used herein, a "HTL precursor cell" is a T lymphocyte that, subsequent to activation, provides helper activity in an immune response such as those listed above for HTL. Activation can be as indicated above for CTL precursor cells. Furthermore, a HTL precursor cell can be a "virgin" T lymphocyte that has never previously been activated or a "memory" T lymphocyte that has previously been activated or the progeny of such a memory T lymphocyte.

A "functional fragment" of a molecule is a fragment of the molecule that is smaller (shorter where the molecule is a polypeptide) than the molecule per se but has at least 10% (e.g., 10%, 20%, 30%, 40%, 50%, 60%, 70%, 80%, 90%, 95%, 98%, 99%, 99.5%, 100% or even more) of the activity of the molecule per se.

As used herein, "operably linked" means incorporated into a genetic construct so that expression control sequences effectively control expression of a coding sequence of interest.

"Polypeptide," "protein," and "peptide" are used interchangeably and mean any peptide-linked chain of amino acids regardless of post-translational modification. While polypeptides and proteins can be any length, peptides are generally shorter polypeptides or proteins, i.e., shorter than 100 amino acid residues.

As used herein, "immunogenic" means capable of eliciting a functional immune response (e.g., a cytotoxic or helper T cell response or an antibody producing response) in a T or a B precursor cell. As used herein, a B precursor cell is a B lymphocyte that, subsequent to activation, can produce antibody molecules. Activation of a B precursor cell can be, without limitation, by recognition of an antigen by an antigen specific immunoglobulin receptor on the B precursor cell or by a non-specific stimulus, e.g., a B cell mitogen such as lipopolysaccharide or pokeweed mitogen. Thus, a B precursor cell can be a "virgin" B lymphocyte that has never previously been activated or a "memory" B lymphocyte that has previously been activated or the progeny of such a B lymphocyte.

As used herein, "antigenic" means capable of being recognized by an effector lymphocyte or an antibody molecule. Thus a substance is antigenic if it is recognized by an antigen specific receptor on, for example, a CTL, a HTL, or a B lymphocyte producing antibody molecules or by an antibody molecule physically unassociated with a B lymphocyte.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., inducing immune responses in mammalian subjects, will be apparent from the following description, from the drawings and from the claims.

DESCRIPTION OF DRAWINGS

FIGS. 1A and 1B are line graphs showing the cytotoxic activity ("% Specific Lysis") of CTL effector cells (at multiple effector to target ratios) of a human carcinoembryonic antigen- (CEA-) specific CTL cell line against TAP-expressing 221.A2 (FIG. 1A) or TAP-deficient T2 target (FIG. 1B) cells that had been incubated overnight with either the $CEA_{691}$ peptide epitope (10 iM; black circles), the TA $CEA_{691}$-HIVtat (10 iM; white circles), or medium alone (black diamonds). Data shown are the means of triplicate values; standard deviations were in no case greater than 10% of the mean values.

FIGS. 6A-6D are fluorescence flow cytometric histograms showing the expression of $H-2K^b/OVA_{257}$ complexes on TAP-expressing EL-4 cells (FIGS. 6A and 6B) or TAP-deficient T2/$K^b$ cells (FIGS. 6C and 6D) that had been incubated overnight with 10 μM of the TA $OVA_{257}$-HIVtat (FIGS. 6A and 6C) or the TA HIVtat-$OVA_{257}$ (FIGS. 6B and 6D). Prior to (for one hour) and during this incubation, the cells were exposed to either medium containing the proteasomal inhibitor lactacystin (10 μM; thick lines) or medium without lactacystin (grey stippled area). Presence on the cell surface of $H-2K^b/OVA_{257}$ complexes was detected with the monoclonal antibody 25D1.16, which is specific for the complexes. Control samples stained with an isotype control antibody are represented by thin lines.

FIGS. 7A-7D are fluorescence flow cytometric histograms showing the expression of $H-2K^b/OVA_{257}$ complexes on TAP-expressing EL-4 cells (FIGS. 7A and 7B) or TAP-deficient T2/$K^b$ cells (FIGS. 7C and 7D) that had been incubated overnight with 10 μM of the TA $OVA_{257}$-HIVtat (FIGS. 7A and 7C) or the TA HIVtat-$OVA_{257}$ (FIGS. 7B and 7D). Prior to (for one hour) and during this incubation, the cells were exposed to either medium containing the endosomal protease inhibitor Peptstatin (100 μM; thick lines) or medium without Pepstatin (grey stippled area). Presence on the cell surface of $H-2K^b/OVA_{257}$ complexes was detected with the monoclonal antibody 25D1.16 which is specific for the complexes. Control samples stained with an isotype control antibody are represented by thin lines.

FIGS. 8A-8F are fluorescence flow cytometric histograms showing the expression of $H-2K^b/OVA_{257}$ complexes on TAP-expressing EL-4 cells (FIGS. 8A, 8B, and 8C) or TAP-deficient T2/$K^b$ cells (FIGS. 8D, 8E, and 8F) that had been incubated overnight with 10 μM of the $OVA_{257}$ peptide epitope (FIGS. 8A and 8D), the TA $OVA_{257}$-HIVtat (FIGS. 8B and 8E), or the TA HIVtat-$OVA_{257}$ (FIGS. 5C and 8F). Prior to (for one hour) and during this incubation, the cells were exposed to either medium containing the furin inhibitor decRVKR-CMK (60 μM; thick lines) or medium without decRVKR-CMK (grey stippled area). Presence on the cell surface of $H-2K^b/OVA_{257}$ complexes was detected with the monoclonal antibody 25D1.16 which is specific for the complexes. Control samples stained with an isotype control antibody are represented by thin lines.

FIG. 10A), the 2C peptide epitope (FIG. 10B), or an LCMV peptide epitope (FIG. 10C) against TAP-deficient RMA-S target cells that had been incubated overnight with the indicated concentrations of either the peptide $OVA_{257}$ peptide epitope (FIG. 10A; "closed diamonds"), the 2C epitope (FIG. 10B: "closed inverted triangles"), the LCMV peptide epitope (FIG. 10C: "open diamonds"), the TA TA3-A ("closed circles"), the TA TA3-B ("closed squares"), the TA TA3-C ("open circles"), or the TA TA3-D ("closed triangles"). The CTL were generated by activation with the relevant peptide epitope of T cells from transgenic mice expressing transgenes encoding TCR specific for the appropriate $H-2K^b$/peptide epitope complexes. Data shown are the means of triplicate values; standard deviations were in no case greater than 10% of the mean values.

DETAILED DESCRIPTION

Figures 2A, 2B, 2C:
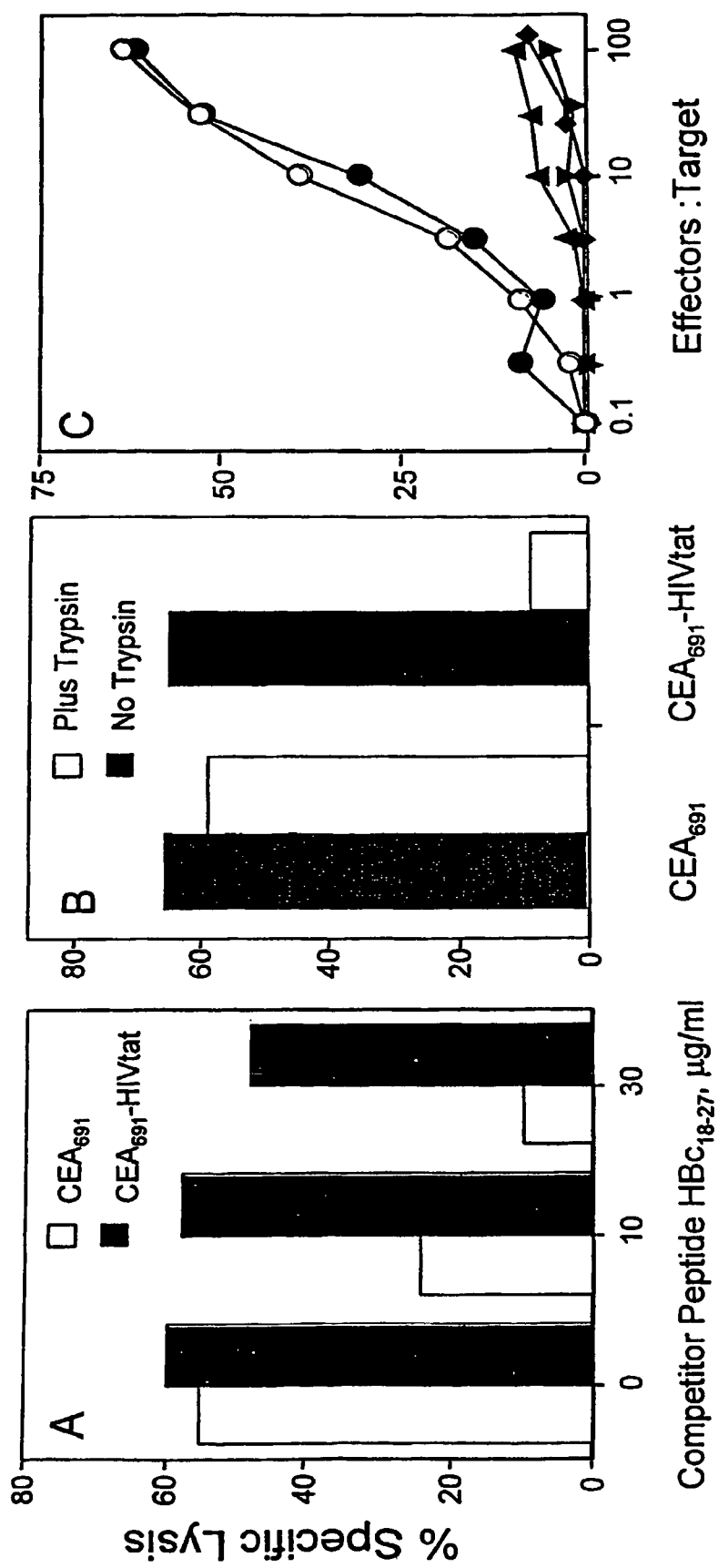
FIG. 2A is a bar graph showing the cytotoxic activity ("% Specific Lysis") of CTL effector cells (at an effector to target ratio of 20:1) of a human CEA-specific CTL cell line against TAP-deficient T2 target cells that had been incubated for 30 minutes with either the $CEA_{691}$ peptide epitope (1 μM; white bars) or the TA $CEA_{691}$-HIVtat (1 μM; black bars). Prior to (for 30 minutes) and during this incubation, the T2 target cells were exposed to the indicated concentrations of the competitor peptide $HBc_{18-27}$.
FIG. 2B is a bar graph showing the cytotoxic activity ("% Specific Lysis") of CTL effector cells (at an effector to target ratio of 20:1) of a human CEA-specific CTL cell line against TAP-deficient T2 target cells that had been incubated for 30 minutes with either the $CEA_{691}$ peptide epitope (1 μM) or the TA $CEA_{691}$-HIVtat (1 μM). Prior to this incubation, the peptide epitope and the TA were pre-incubated at 37° C. in medium either with trypsin (50 mg/ml; white bars) or without trypsin (black bars).
FIG. 2C is line graph showing the cytotoxic activity ("% Specific Lysis") of CTL effector cells (at an effector to target ratio of 20:1) of a human CEA-specific CTL cell line TAP-deficient T2 target cells that had been incubated overnight with either 10 μM of the TA $CEA_{691}$-HIVtat (black circles), the TA HIVtat-$CEA_{691}$ (white circles), the TA $CEA_{691}$-KKK (black triangles), the TA $CEA_{601}$-RRR (inverted black triangles), or the TA $CEA_{691}$-RKK (black diamonds). Data shown in FIGS. 2A-C are the means of triplicate values; standard deviations were in no case greater than 10% of the mean values.
Figures 3A, 3B:
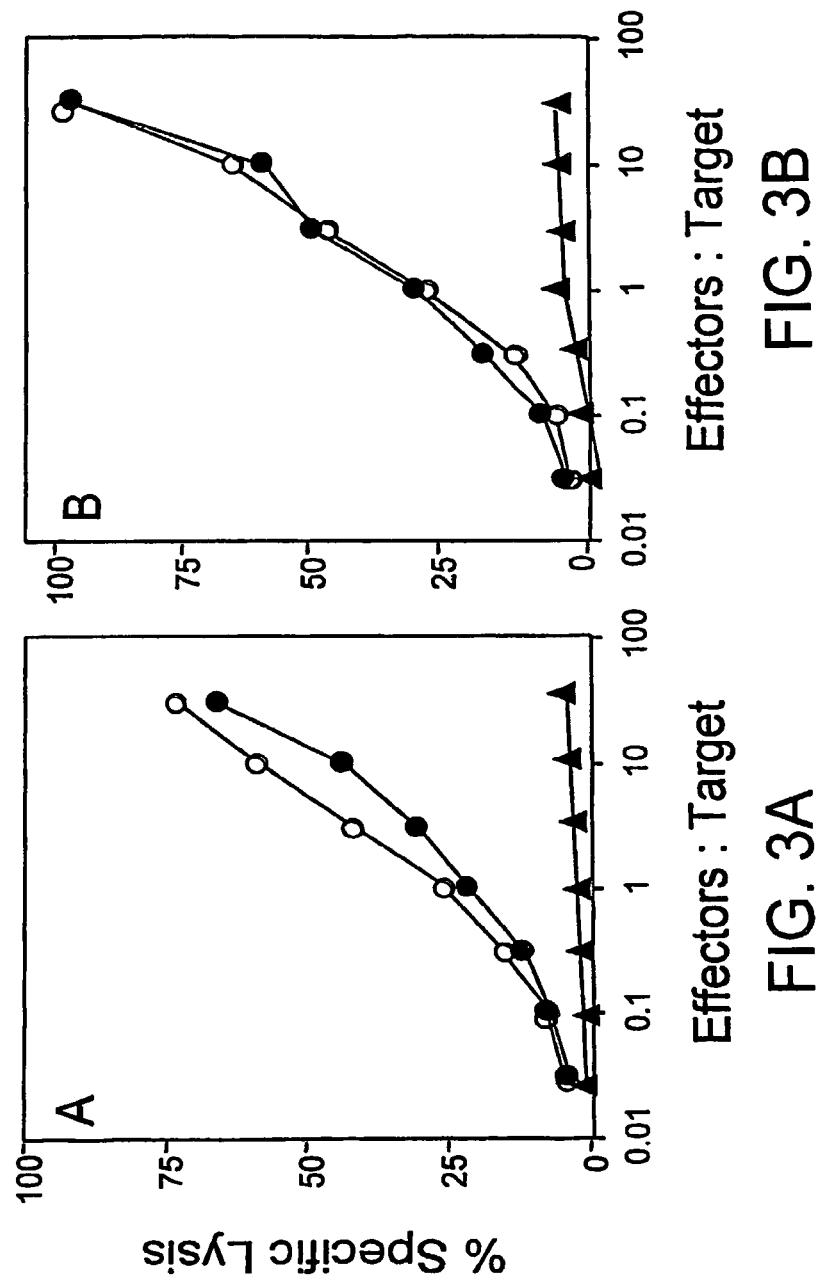
FIGS. 3A and 3B are line graphs showing the cytotoxic activity ("% Specific Lysis") of CTL effector cells (at multiple effector to target ratios) of a melanoma gp100-specific CTL cell clone against TAP-expressing 221.A2 (FIG. 3A) or TAP-deficient T2 (FIG. 3B) target cells that had been incubated overnight with either the $gp100_{209}$ melanoma peptide epitope (10 μM; black circles), the recombinant TA AntpHD-$gp100_{209}$ (10 iM; white circles), or medium alone (black triangles). Data shown are the means of triplicate values; standard deviations were in no case greater than 10% of the mean values.
Figure 4:
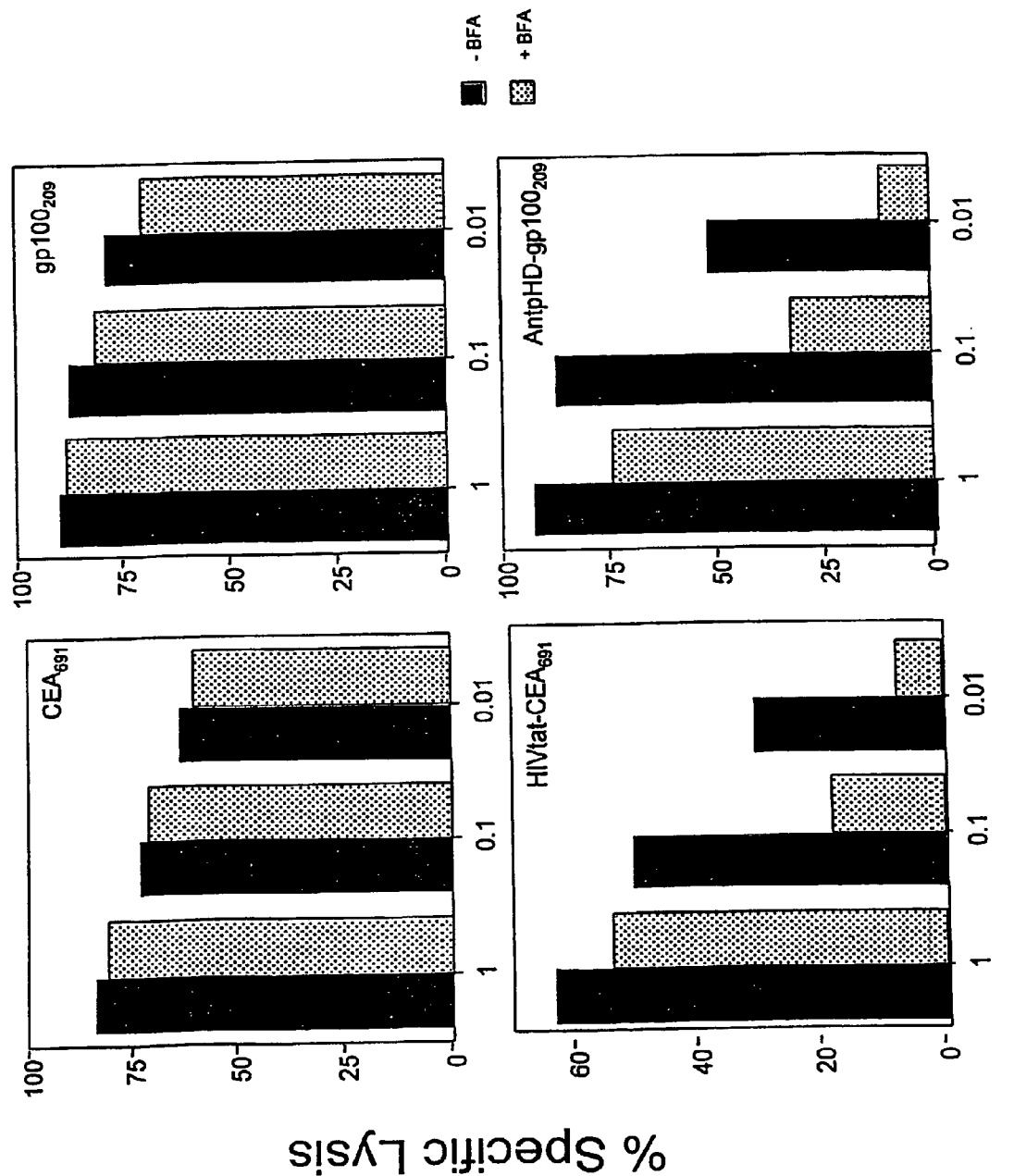
FIG. 4 is a set of four bar graphs showing the cytotoxic activity ("% Specific Lysis") of CTL effector cells (at an effector to target ratio of 20:1) of either a human CEA-specific CTL cell line (left panels) or a melanoma gp100-specific CTL cell clone (right panels) against TAP-deficient T2 target cells that had been incubated for 30 minutes with the indicated three concentrations of "Antigen" (either the $CEA_{691}$ peptide epitope (top left), the TA HIVtat-$CEA_{691}$ (bottom left), the $gp100_{209}$ melanoma peptide epitope (top right), or the recombinant TA AntpHD-$gp100_{209}$ (bottom right)). Prior to (for 30 minutes) and during this incubation (as well as an incubation to label the target cells with $^{51}Cr$), the T2 target cells were exposed to either medium containing brefeldin-A (BFA; 1 μg/ml; stippled bars) or medium without BFA (black bars). No cytotoxicity was observed on targets not exposed to an Antigen. Data shown are the means of triplicate values; standard deviations were in no case greater than 10% of the mean values.
Figures 5A, 5B:
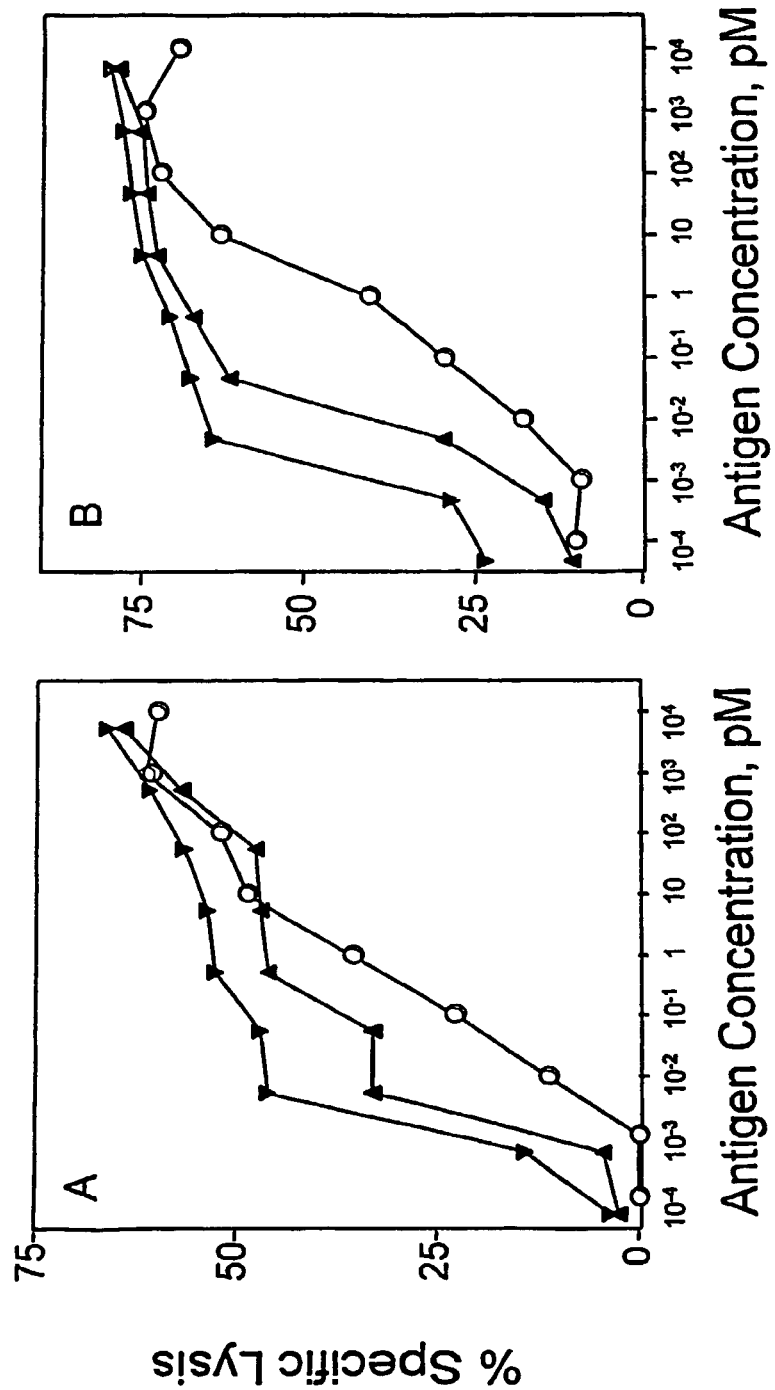
FIGS. 5A and 5B are line graphs showing the cytotoxic activity ("% Specific Lysis") of $OVA_{257}$-specific, $H-2K^b$-restricted CTL (at an effector to target ratio of 20:1) against TAP-expressing EL4 (FIG. 5A) or TAP-deficient T2/$K^h$ target (FIG. 1B) cells that had been incubated for 30 minutes with various concentrations of either the $OVA_{257}$ peptide epitope (white circles), the TA $OVA_{257}$-HIVtat (black triangles), or the TA HIVtat-$OVA_{257}$ (inverted black triangles). Data shown are the means of triplicate values; standard deviations were in no case greater than 10% of the mean values.

The inventors observed that a TA containing a membrane translocating domain (TD) and a T cell epitope was able to sensitize target cells for cytolysis by CTL. Experiments showed that this ability of the TA was not dependent on the action of extracellular proteases or intracellular transporter (TAP) molecules previously shown to transport peptides from the cytoplasm into the ER. The ability of the TA to sensitize the target cells for lysis was dependent on the membrane translocating activity of TD of the TA. Data obtained from these experiments also indicated that the TA needed to enter the target cell and be processed within it in order to sensitize the target cell for lysis and sensitization did not depend on the action of TAP peptide transporter molecules. Experiments with TA containing a peptide epitope and, at the peptide epitope's C terminus, a sequence of three positively charged amino acids (KKK, RRR, or RKK) indicated that a concentration of positively charged amino acids at one end of the TA was not per se sufficient for translocation of the molecule into target cells and thereby sensitize them to lysis by CTL. It seems likely that the other factors (e.g., the length of the TD and/or properties of non-positively charged amino acids in the TD) are necessary for translocating activity. Similar results were obtained with TA containing different CTL epitopes and TD.

Inhibition experiments with the drug brefeldin-A (BFA) indicated that sensitization of target cells involves translocation of the TA from the cytoplasm of the target cell into the ER where the TA can be "trimmed" by appropriate peptidases and the resulting peptide epitopes become associated with MHC molecules to form peptide-MHC molecular complexes which are then exported to the Golgi. Confocal microscopy studies indicated the presence within the ER and Golgi of TAP-expressing and non-expressing target cells of peptide-MHC class I molecular complexes containing an appropriate peptide after exposure of the cells to a TA. Experiments with other proteolytic and metabolic inhibitors indicated that proteolytic processing of the TA does not take place in the cytoplasm or the endocytic compartment, but probably the ER and/or the Golgi. Experiments with an inhibitor of the trans-Golgi family of enzymes known as furins indicated that, provided the TA contained the appropriate furin recognition motifs, significant processing of the TA occurs in the trans-Golgi by the action of the furins. However the data also indicate the participation of other ER and/or Golgi proteolytic enzymes in the processing of the TA involving furins and not involving furins. It is not clear whether peptides that are processed in the Golgi associate with MHC class I molecules there or whether, subsequent to processing, they are transported back to the ER and there associate with the MHC class I molecules. The invention is, however, not limited by any particular mechanism of action.

Thus, it seems that by including recognition sites for other proteolytic enzyme(s) in a TA, one can involve the relevant enzyme(s) in the processing of the TA.

The above described property of furin enzymes was exploited in a TA containing three distinct CTL peptide epitopes separated by furin recognition sites and a TD at the C-terminus. The TA was shown to sensitize target cells for CTL lysis by CTL. The TA was tested for its ability to sensitize TAP-deficient target cells for lysis by CTL from transgenic mice expressing transgenes encoding TCR specific for the relevant CTL peptide epitopes bound to appropriate MHC class I molecules. In this experiment the CTL were activated with the T cell mitogen Concanavalin A (ConA). The same result was obtained with a second TA that was identical to the first except that the linear order of the three peptide epitopes in the TA was changed. In a second experiment in which the CTL were activated not by ConA but by the peptide epitope for which their transgenic T cell is specific, the TA was found to sensitize the target cells for lysis by CTL specific for all three peptide epitopes. It was noted that activation by the peptide epitopes resulted in much higher levels of CTL activity than did activation with ConA.

Most importantly, experiments with three peptide epitope TAs elicited potent CTL responses specific for all three epitopes when injected into normal mice. Where the peptide epitopes were weakly immunogenic, responses were observed using TA but not with the peptide epitopes themselves.

The above findings indicate that TA containing a TD and several peptide epitopes separated by cleavage sites (e.g., proteolytic enzyme cleavage sites) are effective at eliciting CTL responses. Such TA could contain two or more copies of the same peptide epitope and, as such, be efficient deliverers of a single epitope to the appropriate processing compartment of an APC or a target cell. Alternatively, the TA can contain one or more different T cell peptide epitopes and one or more other biologically active agents, e.g., a helper T cell peptide epitope or a cytokine molecule. Thus, the TA of the invention are useful, for example, for activating immune responses (preferably protective immune responses) against one or more peptide epitopes derived, for example, from pathogen- or tumor-associated polypeptides.

Fusion Agents

The fusion agents of the invention contain a TD, a T cell peptide epitope, at least one biologically active agent, and at least two cleavage sites.

Translocation Domains (TD)

The TD to be used in the fusion agents of the invention can be the whole of the signal peptide or some other membrane translocating effector domain of a naturally occurring polypeptide. Alternatively, the TD can be an active fragment of such a signal peptide or membrane translocating effector domain. Examples of such TD include the HIVtat transduction domain (RKKRRQRRR; SEQ ID NO: 1), the Antennapedia homeodomain (AntpHD) protein tanslocating sequence (RQIKIWFPNRRMKWKK; SEQ ID NO:2) or an active fragment of such sequences. Other naturally amino acid sequences of interest, all or part of which can be used in as TD in the fusion agents of the invention, include hydrophobic sequences (e.g., MAISGVPVLGFFHAVLMSAQESWA; SEQ ID NO:3) that are typically found at the N-terminus of proteins destined for the ER. The peptide sequence KDEL (SEQ ID NO:4) which has been shown to act as an ER retention signal can also be useful as all or part of a TD of the invention. In addition, the amino acid sequence KFERQ (SEQ ID NO:5) (and closely related sequences) are known to target polypeptides containing them to lysosomes and other amino acid sequences (e.g., MDDQRDLISNNEQLP) (SEQ ID NO:6) target relevant polypeptides to endosomes. Other amino acid sequences useful as TD in the fusion agents of the invention can be derived from fibroblast growth factor [Lin et al. (1995) J. Biol. Chem. 270:14255-14258], Galparan (transportan) [Pooga et al. (1998) FASEB. J. 12:67-77], and HSV-1 structural protein VP22 [Elliott et al. (1997) Cell 88:223-233]. It is understood that the TD can contain all or part of one or more naturally occurring membrane translocating effector regions. All that is required is that fusion agents containing such TD be able to render cells into which they are incorporated immunogenic and/or antigenic. Methods of assessing the immunogenicity or antigenicity of such TA are known in the art, e.g., the methods described in the Examples provided herein.

In addition to the naturally occurring amino acid sequences, the fusion agents can contain TD composed of artificial amino acid sequences. For example, poly-Arginine (pol-R) sequences can be used. Such poly-R sequences generally contain 7 to 20 (e.g., 7 to 15) R residues. Instead of arginine, analogs of arginine having longer side chains than arginine can be used. In these analogs, instead of three methylene groups (as in arginine), there can be 4-10 (e.g., 4, 5, 6, 7, 8, 9 or 10) methylene groups [Wender et al. (2000) Proc. Nat'l. Acad. Sci. U.S.A. 97:13003-13008]. Other synthetic TD are described in detail in International Application No. PCT/US98/10571.

The TD can be at the N or C terminus of the fusion agents of the invention. In addition, the TD can be any of the above-listed amino acid sequences but using D-rather than L-amino acids, and/or with their amino acid sequences reversed. Methods to test the optimal structural characteristics of TD are known to skilled artisans, e.g., those or obvious modifications of those described in the Examples provided herein.

Peptide Epitopes

The peptide epitopes included in the fusion agents of the invention can be any peptide epitope recognized by an effector T cell or a precursor of an effector T cell when the peptide epitope is complexed with an MHC molecule. The invention is not limited by: (a) the T cell having any particular phenotype (e.g., CD4+ or CD8+) or function (e.g., cytotoxicity, helper activity, immune deviating activity, or suppressive activity); or (b) the MHC being of any particular class. While the majority of T cells with cytotoxic activity are CD8+ and recognize peptide epitopes bound to MHC class molecules, CD4+ CTL that recognize antigenic peptides bound to MHC class II molecules are known in the art. CD4+ CTL that recognize peptides bound to MHC class I molecules and CD8+ CTL that recognize antigenic peptides bound to MHC class II molecules have also been described. In addition, while the majority of T cells with helper and/or immune deviating activity are CD4+ T cells and recognize antigenic peptides bound to MHC class II molecules, these activities have also been observed in MHC class I restricted CD8+ T cells. Similarly, while most immunosuppressive T cells are CD8+ T cells, CD4+ T cells with immunosuppressive activity have also been demonstrated. The invention includes fusion agents containing peptide epitopes recognized by all these T cells. Preferred peptide epitopes will be those recognized by MHC class I restricted CTL and MHC class II restricted CD4+ helper/immune deviating T cells. Peptide epitopes recognized by MHC class I restricted epitopes are particularly preferred.

Peptide epitopes that can be included in the fusion agents can be derived, for example, from any of a wide range of microbial (e.g., bacterial, fungal, yeast, viral or parasite such as protozoan parasite) proteins. Examples of relevant microorganisms include, without limitation, *Mycobacteria tuberculosis, Salmonella enteriditis, Listeria monocytogenes, M. leprae, Staphylococcus aureus, Escherichia coli, Streptococcus pneumoniae, Borrelia burgdorferi. Actinobacillus pleuropneumoniae, Helicobacter pylori, Neisseria meningitidis, Yersinia enterocolitica, Bordetella pertussis, Porphyromonas gingivalis, mycoplasma, Histoplasma capsulatum, Cryptococcus neoformans, Chlamydia trachomatis, Candida albicans, Plasmodium falciparum, Entamoeba histolytica, Toxoplasma brucei, Toxoplasma gonadii, Leishmania major*, human immunodeficiency virus 1 and 2, influenza virus, measles virus, rabies virus, hepatitis virus A, B, and C, rotaviruses, papilloma virus, respiratory syncytial virus, feline immunodeficiency virus, feline leukemia virus, and simian immunodeficiency virus. Examples of relevant microbial proteins include, without limitation, the B subunit of heat labile enterotoxin of *E. coli* [Konieczny et al. (2000) FEMS Immunol. Med. Microbiol. 27(4):321-332], heat-shock proteins, e.g., the *Y. enterocolitica* heat shock protein 60 [Konieczny et al. (2000) supra; Mertz et al. (2000) J. Immunol. 164(3):1529-1537] and *M. tuberculosis* heat-shock proteins hsp60 and hsp70, the *Chlamydia trachomatis* outer membrane protein [Ortiz et al. (2000) Infect. Immun. 68(3):1719-1723], the *B. burgdorferi* outer surface protein [Chen et al. (1999) Arthritis Rheum. 42(9):1813-1823], the *L. major* GP63 [White et al. (1999) Vaccine 17(17):2150-2161 (and published erratum in Vaccine 17(20-21):2755)], the *N. meningitidis* meningococcal serotype 15 PorB protein [Delvig et al. (1997) Clin. Immunol. Immunopathol. 85(2); 134-142], the *P. gingivalis* 381 fimbrial protein [Ogawa, (1994) J. Med. Microbiol. 41(5):349-358], the *E. coli* outer membrane protein F [Williams et al. (2000) Infect. Immun. 68(5):2535-2545], influenza virus hemagglutinins and neuramindases, retroviral (e.g., HIV) surface glycoproteins (e.g., HIV gp160/120), or retroviral tat or gag proteins. CTL are by virtue of their ability to kill target cells infected with any of a wide variety of intracellular pathogens (e.g., viruses, or intracellular bacteria and protozoans) potent mediators of immunity to such pathogens. Thus, since the fusion agents of the invention are efficient activators of CTL responses, they can be efficient vaccines and/or therapeutic agents in infections with such intracellular pathogens. In addition, helper T cells release a wide variety of cytokines that mediate pathogen-destructive inflammatory responses.

Furthermore, peptide epitopes can be derived from a wide variety of tumor-associated antigens (TAA). As used herein, a "TAA" is a molecule (e.g., a protein molecule) that is expressed by a tumor cell and either (a) differs qualitatively from its counterpart expressed in normal cells, or (b) is expressed at a higher level in tumor cells than in normal cells. Thus, a tumor antigen can differ (e.g., by one or more amino acid residues where the molecule is a protein) from, or it can be identical to, its counterpart expressed in normal cells. It is preferably not expressed by normal cells. Alternatively, it is expressed at a level at least two-fold higher (e.g., a two-fold, three-fold, five-fold, ten-fold, 20-fold, 40-fold, 100-fold, 500-fold, 1,000-fold, 5,000-fold, or 15,000-fold higher) in a tumor cell than in the tumor cell's normal counterpart. Examples of relevant cancers include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such ovarian cancer, vaginal cancer, bladder cancer, testicular cancer, prostate cancer or penile cancer, bone tumors, and vascular tumors. Relevant TAA include, without limitation, carcinoembryonic antigen (CEA), prostate specific antigen (PSA), MAGE (melanoma antigen) 1-4, 6 and 12, MUC (mucin) (e.g., MUC-1, MUC-2, etc.), tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP) Bcl-2, and Ki-67. Both CTL and helper T cells have been shown to be efficient effectors of tumor immunity. Other peptide epitopes that can be'included in the fusion agents of the invention are those derived from autoantigenic polypeptides that are involved in the initiation or progression of autoimmune diseases. Examples of such autoimmune diseases include rheumatoid arthritis (RA), multiple sclerosis (MS), insulin-dependent diabetes mellitus (IDDM), muscular dystrophy (MD), myasthenia gravis (MG), and systemic lupus erythematosus (SLE). Examples of appropriate autoantigenic polypeptides include, without limitation: (a) in regard to MS (or experimental autoimmune encephalitis), myelin basic protein (MBP), proteolipid protein (PLP), myelin oligodendrocyte protein (MOG), and alpha B-crystallin; (b) in regard to RA, collagen; (c) in regard to MG, the acetylcholine receptor; (d) in regard to SLE, the Smith protein, RNP ribonucleoprotein, and SS-A and SS-B proteins; and (e) in regard to IDDM, insulin/proinsulin, glutamic acid decarboxylase (65 kD isoform; GAD-65), and IA-2. Other autoimmune diseases and polypeptides that have been implicated as autoantigens involved in their genesis are listed below:

Autoimmune ovarian failure: 3β hydroxysteroid dehydrogenase

Graves' thyroiditis: thyroglobulin, thyroid peroxidase, and thyroid stimulating hormone receptor Hashimoto's thyroiditis: thyroglobulin and thyroid peroxidase Primary hypothyroidism: thyroglobulin and thyroid peroxidase Coeliac disease: transglutaminase Primary biliary cirrhosis: pyruvate dehydrogenase Autoimmune hepatitis: cytochrome P4502D6

Addison's disease: 21α hydroxylase

Vitiligo: tyrosinase

Anti-glomerular basement membrane disease (Goodpasture's syndrome): type IV collagen Systemic sclerosis: Scl-70

While immunizing with peptide epitopes derived from such autoantigens might at first glance appear likely to exacerbate or cause earlier onset of relevant autoimmune diseases, administration of some peptide epitopes derived from these polypeptides has been found to result in either direct tolerization of autoimmune effector cells (e.g., T and/or B lymphocytes) or "immune deviation" from a pathogenic autoimmune response towards an nonpathogenic or possibly even a protective autoimmune response. Of particular interest with respect to immune deviation are altered peptide ligands (APL).

An APL is a variant peptide epitope in which one or more (e.g., 1, 2, 3, 4, 5, or 6) amino acid residues of a parent wild-type peptide epitope that activates a response in T cells (CD4+ or CD8+) have been changed. In an APL used in the fusion agents of the invention, fewer than half of the residues of the wild-type peptide are changed, e.g., fewer than 50%, fewer than 40%, fewer than 30%, fewer than 25%, fewer than 20%, fewer than 15%, fewer than 10%, or fewer than 5%. Thus, for example, in an APL derived from a wild-type peptide 20 amino acids long and differing from the wild-type peptide at 6 positions, 30% of the amino acids of the wild-type peptide are changed. Alternatively, in an APL derived from a wild-type peptide 15 amino acids long and differing from the wild-type peptide at 3 positions, 20% of the amino acids of the wild-type peptide are changed.

An APL retains at least some ability to bind to the MHC (class I or class II) molecule to which the parent peptide epitope binds and at least some ability to be recognized by the antigen-specific T lymphocyte receptor(s) of the T cell(s) that recognize the parent peptide bound to the same type of MHC molecule. However, by definition, the APL activates a response in the T cells that is qualitatively different from that activated by the parent peptide epitope. For example, while the parent peptide epitope can activate a helper T cell 1- (Th1-) type response in which the cytokines interleukin-2 (IL-2), interferon-γ (IFN-γ), and tumor necrosis factor-α (TNF-α) are produced by the activated T cells, an APE derived from this parent peptide epitope might instead activate a helper T cell 2- (Th2-) type response in the T cells. In a Th2 response, the cytokines interleukin-4 (IL-4), interleukin-5 (IL-5), and interleukin-10 (IL-10) are produced by the activated CD4+ T cells. Alternatively, if a particular parent peptide epitope elicits a Th2 response in a given T cell, an APL derived from the parent peptide could activate a Th1 response in the T cell. Some APL have been shown to switch a Th1 response to a Th0 response in which both Th1- and Th2-type cytokines are produced. Furthermore, an APL could redirect a $CD4^+$ T cell response towards a Th3-type response in which the predominant cytokine produced is transforming growth factor-β (TGF-β) TGF-β has been shown to be suppressive of a wide range of immune responses.

In general, Th1 responses are associated with cell-mediated immune responses and Th2 responses are associated with antibody- (i.e., B cell-)mediated immune responses. Thus, the relative number of CD4+ T cells responding in a Th1- versus a Th2-type fashion will determine the nature (cell-mediated versus antibody-mediated) of the immune response generated by an antigen in a particular individual. Some conditions, and in particular autoimmune diseases (e.g., RA, IDDM, and MS), have been shown to be due to cellular immune responses and thus to be dependent on Th1 $CD4^+$ T cell responses. Other diseases (e.g., MG and SLE) have been shown to be mediated by antibody (i.e., B-cell) responses, and thus to be dependent on Th2 $CD4^+$ T cell responses. Thus, a fusion agent containing an APL that serves to direct a $CD4^+$ T cell response from a Th1 to a Th2 response can be useful in treatment or prevention of the first category of diseases and fusion agent containing an APL that serves to alter a $CD4^+$ T cell response in a Th2 to Th1 direction can be useful in the treatment or prevention of the second category of diseases.

The amino acid substitutions in an APL can be radical. For example, an amino acid with a positively charged side chain (e.g., lysine) can be replaced by an amino acid with a negatively charged side chain (e.g., aspartic acid) or a hydrophobic side chain (e.g., isoleucine) and vice versa. In addition, an amino acid with a bulky side chain (e.g., tryptophan) can be replaced with an amino acid with small side chain (e.g., glycine or alaninc) and vice versa. Alternatively, the substitutions can be conservative. For example, a negatively charged amino acid can be replaced with another negatively charged amino acid (e.g., aspartic acid with glutamic acid) or one hydrophobic amino acid with another hydrophobic amino acid (e.g., leucine with valine or isoleucine).

The peptide epitopes to be used in the fusion agents of the invention can be of a variety of lengths. The size range of peptides that bind to MHC class I molecules is 8-12 amino acid residues. Thus, fusion agents designed to activate MHC class I restricted T cell responses can contain peptide epitopes 8-12 amino acid residues long. The size range of peptides that bind to MHC class II molecules is 9-30 (e.g., 9-20) amino acid residues. Thus, fusion agents designed to activate MHC class I restricted T cell responses can contain peptide epitopes 9-30 (e.g., 9-20) amino acid residues long. However, since the peptide epitopes can be "trimmed" by intracellular proteases once they have entered the cell, there is effectively no upper limit on the size of the peptide epitopes in the fusion agents of the invention. Thus, the peptide epitopes can be, for example, 7-50 (e.g., 7, 8, 9, 10, 11, 12, 13, 14, 15, 16, 17, 18, 19, 20, 21, 22, 23, 24, 25, 26, 27, 28, 29, 30, 32, 34, 36, 38, 40, 45, or 50) amino acid residues long.

Biologically Active Agents

The fusion agents contain (in addition to a TD, cleavage sites, and a T cell peptide epitope) one or more biologically active agents. The biologically active agent can be an additional one or more of any of the peptide epitopes described above. Thus, the fusion agents can contain two or more (e.g., two, three, four, five, six, seven, eight, nine, ten, 11, 12, 13, 14, 15, 16, 17, 18, 19, 20, 25, 30, 40, or 50) copies of the same peptide epitope and, as such, be efficient deliverers of a single epitope to the appropriate processing compartment of an APC or a target cell. Alternatively, the TA can contain one or more (as above) copies of one or more (e.g., two, three, four, five, six, seven, eight, nine, ten, 11, 12, 13, 14, 15, 16, 17, 18, 19, or 20) different CTL peptide epitopes. Where the TA contain different peptide epitopes, such epitopes can be derived from the same polypeptide or different polypeptides.

Alternatively, the biologically active agents can be, for example, immune-enhancing molecules or functional fragments of such immune-enhancing molecules. Examples of immune enhancing molecules are cytokines, and chemokines (e.g., MIP-1α, MIP-3β, and RANTES). Appropriate cytokines include interleukin- (IL-)1, IL-2, IL-3, IL-4, IL-5, IL-6, IL-7, IL-8, IL-10, IL-12, IL-13, IL-15, interferon- (IFN-) α, β or γ, granulocyte- colony stimulating factor (G-CSF), macrophage colony stimulating factor (M-CSF), or granulocyte macrophage-colony stimulating factor (GM-CSF).

Cleavage Sites

Generally, the fusion agents contain cleavage sites between the TD and the peptide epitope or between the TD and the additional biologically active agent (depending on whether the TD is next to the peptide epitope or an additional biologically active agent), between the peptide epitope and between a first biologically active agent, and between all additional biologically active agents in fusion agent. Instead of a discrete cleavage site after the TD, the TD can include all or part of a cleavage site. For example, the HIVtat transduction domain (RKKRRQRRR; SEQ ID NO:1), which as recited above can be used as a TD in the fusion agents of the present invention, includes 2 furin recognition sequences. Furin enzymes recognize sites having the following amino acid motif: RX(R/K)R (SEQ ID NO:7) where X can be any amino acid. Other enzymes within the family of subtilisin-like pro-protein convertases recognize sites having the amino acid motif RXXR, X again being any amino acid. Thus, useful cleavage sites can have this RXXR sequence.

Cleavage sites will preferably be proteolytic enzyme recognition sequences, e.g., a sequence recognized, by the furin family of enzymes (see above). Other cleavage sites include disulfide bond-containing agents which are cleaved by reducing agents such a glutathione. Examples of such reducible cleavage sites include N-acetyl-protected cysteine residues. Cleavage sites can also be photocleavable cleavage sites which are cleaved upon exposure to electromagnetic radiation. Examples of such photocleavable cleavage sites include meta-nitrobenzoate moieties. Other examples of reduction-cleavable and photocleavable sites can be found in International Application No. PCT/US98/10571 and the Pierce Products (Rockford, Ill.) Catalog.

Smaller fusion agents (fewer than 100 amino acids long) can be conveniently synthesized by standard chemical means. In addition, both small and large polypeptides can be produced by standard in vitro recombinant DNA techniques, and in vivo transgenesis using the nucleotide sequences encoding the appropriate polypeptides. Methods well known to those skilled in the art can be used to construct expression vectors containing relevant coding sequences and appropriate transcriptional/translational control signals. See, for example, the techniques described in Sambrook et al., Molecular Cloning: A Laboratory Manual [Cold Spring Harbor Laboratory, N.Y., 1989], and Ausubel et al., Current Protocols in Molecular Biology, [Green Publishing Associates and Wiley Interscience, N.Y., 1989].

The components of the fusion agents can be synthesized as a single unit (by either chemical synthetic or recombinant methods) or as separate entities and then linked together by standard chemical methods known in the art. Where cleavable sites in the fusion agents are moieties other than amino acid sequences, it will generally be desirable to produce the components separately, to incorporate the cleavable moieties at the appropriate ends of the components, and then to link the components together using standard chemical methods.

The TD and peptide epitopes can be polypeptides of any species, e.g., a human, non-human primate (e.g., monkey), mouse, rat, guinea pig, hamster, cow, sheep, goat, horse, pig, rabbit, dog, or cat.

The amino acid sequence of the various components of the fusion agents of the invention can be identical to the wild-type sequences of appropriate components. Alternatively, any of the components can contain mutations such as deletions, additions, or substitutions. All that is required is that the variant fusion agent have at least 5% (e.g., 10%, 20%, 30%, 40%, 50%, 60%, 70%, 80%, 90%, 95%, 99%, 100%, or even more) of the ability of the fusion agent containing only wild-type sequences to the enter a target cell or an APC and render the target cell sensitive to lysis or the APC capable of activating a T cell having the appropriate specificity. Substitutions will preferably be conservative substitutions. Any given component will generally have no more than eight (i.e., not more than: eight, seven, six, five, four, three, two, or one) conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

Fusion agents of the invention also include those described above, but modified for in vivo use by the addition, at either or both the amino- and carboxyl-terminal ends, of a blocking agent to facilitate survival of the relevant fusion agent in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the fusion agent to be administered. This can be done either chemically during the synthesis of the peptide or by recombinant DNA technology by methods familiar to artisans of average skills.

Alternatively, blocking agents such as pyroglumatic acid or other molecules known in the art can be attached to the amino and/or carboxyl terminal residues, or the amino group at the amino terminus or carboxyl group at the carboxyl terminus can be replaced with different moiety. Likewise, the peptides can be covalently or noncovalently coupled to pharmaceutically acceptable "carrier" proteins prior to administration.

Also of interest are peptidomimetic fusion agents that are designed based upon the amino acid sequences of the components of the fusion agents. Peptidomimetic compounds are synthetic, non-peptide compounds having a three-dimensional conformation (i.e., a "peptide motif") that is substantially the same as the three-dimensional conformation of a selected peptide. The peptide motif provides the peptidomimetic compound with the ability to be transported across biological membranes and to activate T cells in a manner qualitatively identical to that of the APL from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. In peptidomimetic fusion agents in which cleavable sites are amino acid sequences cleaved by proteolytic enzymes, the amino acids of the cleavable sites will generally be linked by normal peptide bonds or bonds that do not interfere with the susceptibility of the cleavage site to cleavage by a relevant proteolytic enzyme.

A peptide mimetic of interest can contain, for example, a peptide bond linked poly-glycine backbone with amino acid side chains, or modifications of amino acid side chains (e.g., the arginine analog side chains described above) linked to the N-atom of the amide bonds, thereby avoiding stereogenic centers [Wender et al. (2000), supra]. Such sequences can be used for all of the parts of the fusion agents of the invention. They can be especially useful in the TD of the fusion agents.

Fusion Agent Encoding Nucleic Acids

The invention also features nucleic acid molecules encoding the fusion agents of the invention. These nucleic acid molecules can be cDNA, genomic DNA, synthetic DNA, or RNA, and can be double-stranded or single-stranded (i.e., either a sense or an antisense strand). Segments of these molecules are also considered within the scope of the invention, and can be produced, for example, by the polymerase chain reaction (PCR) or generated by treatment with one or more restriction endonucleases. A ribonucleic acid (RNA) molecule can be produced by in vitro transcription. Preferably, the nucleic acid molecules encode peptides that, regardless of length, are soluble under normal physiological conditions.

The nucleic acid molecules of the invention can contain, as segments encoding the various components of the fusion agents, either naturally occurring sequences or sequences that differ from those that occur naturally, but, due to the degeneracy of the genetic code, encode the relevant fusion agent components. In addition, these nucleic acid molecules are not limited to coding sequences, e.g., they can include some or all of the non-coding sequences that lie upstream or downstream from a coding sequence.

The nucleic acid molecules can be synthesized (for example, by phosphoramidite-based synthesis) or obtained from a biological cell, such as the cell of a mammal. Thus, the nucleic acids can be those of a human, non-human primate (e.g., monkey) mouse, rat, guinea pig, cow, sheep, horse, pig, rabbit, dog, or cat.

The invention encompasses recombinant nucleic acid molecules (for example, nucleic acid molecules encoding any of the fusion agents described herein) incorporated into a vector (for example, a plasmid or viral vector) or into the genome of a heterologous cell (or the genome of a homologous cell, at a position other than the natural chromosomal location). The nucleic acids can also contain segments encoding components with conservative substitutions (see above).

The invention also encompasses: (a) vectors that contain any of the foregoing fusion agent coding sequences and/or their complements (that is, "antisense" sequence); and (b) expression vectors that contain any of the foregoing fusion agent coding sequences operably associated with any transcriptional/translational regulatory element (TRE), such as a promoter or a promoter-enhancer combination, necessary to direct expression of the coding sequences.

A promoter is a TRE composed of a region of a DNA molecule, typically within 100 nucleotide pairs upstream of the point at which transcription starts. Promoters are clustered around the initiation site for RNA polymerase II. Enhancers provide expression specificity in terms of time, location, and level. Unlike a promoter, an enhancer can function when located at variable distances from the transcription site, provided a promoter is present. An enhancer can also be located downstream of the transcription initiation site. The coding sequence in the expression vector is operatively linked to a transcription terminating region. To bring a coding sequence under the control of a promoter, it is necessary to position the translation initiation site of the translational reading frame of the peptide or polypeptide between one and about fifty nucleotides downstream (3') of the promoter. A list of promoters is provided in Table 1.

TABLE 1

TABLE OF PROMOTERS

| PROMOTER TYPE | PROMOTER ELEMENT | REFERENCES |
|---|---|---|
| CONSTITUTIVE | | |
| | β-actin | Liu et al., Mol. Cell Biol. 10:3432-40 (1990) |
| | tubulin | Angelichio et al., Nucleic Acids Res. 19:5037-43 (1991) |
| | CMV | see Invitrogen |
| | SV40 enhancer | see Pharmacia |
| | RSV-LTR | see Invitrogen |
| | Adenovirus enhancer | Inoue et al., Biochem Biophys Res Commun 173:1311-6 (1990) |
| TISSUE-SPECIFIC | | |
| Liver | serum amyloid A | Li et al., Nucleic Acids Res 20:4765-72 (1992) |
| | phenylalanine hydroxylase | Wang et al., J Biol Chem 269:9137-46 (1994) |
| | IGFBP-1 | Babajko et al., PNAS 90:272-6 (1993) |
| | apolipoprotein B | Brooks et al., Mol Cell Biol 14:2243-56 (1994) |
| | albumin | Pinkert et al., Genes Dev 1:268-76 (1987) |
| | vitellogenin | Corthesy et al., Mol Endocrinol 5:159-69 (1991) |
| | angiotensinogen | Brasier et al., Embo J 9:3933-44 (1990) |
| | haptoglobin | Yang et al., Genomics 18:374-80 (1993) |
| | PEPCK | Short et al., Mol Cell Biol 12:1007-20 (1992) |
| | factor IX | Jallat et al., Embo J 9:3295-301 (1990) |
| | transferrin | Idzerda et al., Mol Cell Biol 9:5154-62 (1989) |
| | β-fibrinogen | Dalmon et al., Mol Cell Biol 13:1183-93 (1993) |
| | kininogen | Chen et al., Mol Cell Biol 13:6766-77 (1993) |
| | CRP | Toniatti et al., Mol Biol Med 7:199-212 (1990) |
| KIDNEY | rennin | Fukamizu et al., Biochem Biophys Res Commun 199:183-90 (1994) |
| HEART | cardiac myosin light chain | Lee et al., J Biol Chem 267:15875-85 (1992) |
| | cardiac troponin C | Parmacek et al., Mol Cell Biol 12:1967-76 (1992) |
| | α-cardiac myosin heavy chain | Gulick et al., Biol Chem 266:9180-5 (1991) |
| | MCK | Johnson et al., Mol Cell Biol 9:3393-9 (1989) |
| | troponin I | |
| | atrial natriuretic factor | Rockman et al., PNAS 88:8277-81 (1991) erratum 88(21):9907 |
| LUNG | pulmonary surfactant protein SP-C | Glasser et al. Am J Physiol L349-56 (1991) |
| PANCREAS/ISLET | insulin | Dandoy et al., Nucleic Acids Res 19:4925-30 (1991); and Selden et al., Nature 321:525-8 (1986) |
| | pancreatic amylase | Osborn et al., Mol Cell Biol 7:326-34 (1987) |

TABLE 1-continued

TABLE OF PROMOTERS

| PROMOTER TYPE | PROMOTER ELEMENT | REFERENCES |
|---|---|---|
| BRAIN/GLIA | GFAP | Brenner et al., Neurosci 1030-7 (1994) |
| | JCV | Henson et al., J Biol Chem 269:1046-50 (1994) |
| | MBP | Miskimins et al., Brain Res Dev Brain Res 65:217-21 (1992) |
| | serotonin 2 receptor | Ding et al., Brain Res Mol Brain Res 20:181-91 (1993) |
| | myelin PO | Monuki et al., Mech Dev 42:15-32 (1993) |
| | myelin proteolipid protein | Berndt et al. J Biol Chem 267:14730-7 (1992) |
| INDUCIBLE | | |
| A) IMMUNE SYSTEM/NATURAL | IL-2 | Thompson et al., Mol Cell Biol 12:1043-53 (1992) |
| | IL-4 | Todd et al., J Exp Med 177:1663-74 (1993) |
| | IL-6 | Libermann et al., Mol Cell Biol 10:2327-34 (1990); and Matsusaka et al., PNAS 90:10193-7 (1993) |
| | IL-8 | Matsusaka et al., PNAS 90:10193-7 (1993) |
| | IL-10 | Kim et al., J Immunol 148:3618-23 (1992) |
| | TNF-α | Drouet et al., J Immunol 147:1694-700 (1991) |
| | IL-1 | Shirakawa et al., Mol Cell Biol 13:1332-44 (1993) |
| | MIP-1 | Grove et al., Mol Cell Biol 13:5276-89 (1993) |
| | IFN-γ | Penix et al., J Exp Med 178-1483-96 (1993) |
| | VCAM-1 | Iademarco et al., J Biol Chem 267:16323-9 (1992) |
| | ICAM-1 | Voraberger et al., J Immunol 14:2777-86 (1991) |
| | ELAM-1 | Whelan et al., Nucleic Acids Res 19:2645-53 (1991) |
| | tissue factor | Mackman et al., J Exp Med 174:1517-26 (1991) |
| | IFN-β | Visvanathan et al., Einho J 8:1129-38 (1989) |
| | c-jun | Muegge et al., PNAS 90:7054-8 (1993) |
| | junB | Nakajima et al., Mol Cell Biol 13:3017-41 (1993) |
| | c-fos | Morgan et al., Cell Prolif 25:205-15 (1992) |
| | iNOS | Xic et al., J Exp Med 177:1779-84 (1993) |
| | G-CSF | Shannon et al., Growth Factors 7:181-93 (1992) |
| | GM-CSF | Miyatake et al., Mol Cell Biol 11:5894-901 (1991) |
| B) IMMUNE SYSTEM/SYNTHETIC multiple copies of binding sites | NF-KB | Lenardo et al., Cell 58:227-9 (1989) |
| | NF-IL6 | Akira et al., Embo J 9:1897-906 (1990) |
| | IL6-response element | Wcgenka et al., Mol Cell Biol 13:276-88 (1993) |
| | CRE | Brindle et al., Curr Opin Genet Dev 2:199-204 (1992) |
| | AP-1 | Auwerx et al., Oncogene 7:2271-80 (1992) |
| | p91/stat combinations of multiple NF-KB and NF-IL6 or combinations with the other elements | Larner et al., Science 261:1730-3 (1993) |
| C) EXOGENOUS/ NONMAMMALIAN | IPTG inducible/lac repressor/operon system | see Stratagene LacSwitchŎ, La Jolla, CA |
| | ecdysone-inducible promoter/ecdysone receptor | Burtis et al., Cell 61:85-99 (1990) |
| | Na-salicylate-inducible promoter PG/regulator nahR | Yen, J Bacteriol 173:5328-35 (1991) |
| | nalidixic acid inducible recA promoter | Rangwala et al., Biotechnology 9:477-9 (1993) |

Suitable expression vectors include, without limitation, plasmids and viral vectors such as herpes viruses, retroviruses, vaccinia viruses, attenuated vaccinia viruses, canary pox viruses, adenoviruses, adeno-associated viruses, lentiviruses and herpes viruses, among others.

The expression vectors of the invention containing the above described coding sequences have a variety of uses. They can be used, for example, to transfect or transduce either prokaryotic (e.g., bacteria) cells or eukaryotic cells (e.g., yeast, insect, or mammalian) cells. Such cells can then be used, for example, for large or small scale in vitro production of the relevant fusion protein by methods known in the art (see above). In essence, such methods involve culturing the cells under conditions which maximize production of the fusion agents and isolating the fusion agents from the culture, i.e., from the cells and/or from the culture medium. The transduced/transfected cells can be used as cells for delivery of the fusion agent to a host target cell by administration of the transduced/transfected cells to a subject harboring the target cell. Alternatively, the vector itself can be delivered to the subject.

Methods of Activating an Immune Response

The invention features methods of activating mammalian immune responses in which cells of the immune system are exposed to one or more fusion agents of the invention. An advantage of the fusion agents is that immune responses either to a single epitope or to multiple peptide epitopes can be activated in a mammal by contacting cells of the immune system of the mammal with a single agent. This is possible since the fusion agents can contain multiple (two or more) copies of a single peptide epitope, a single copy of multiple (two or more) peptide eiptopes, one or more copies of one or more peptide eiptopes together with one or more copies of any of the above-listed non-peptide epitope biologically active agents listed above. The fusion agents of the invention are particularly useful for introducing peptide epitopes into APC in order to generate a MHC class I restricted T cell response. Such responses are typically only generated by recognition of peptide epitopes produced by processing of polypeptides synthesized within an appropriate APC. In addition, a fusion agent of the invention can also be useful for sensitizing target cells for lysis by CTL with specificity for one or more peptide epitopes that the fusion agent contains.

The methods of the invention can be performed in vitro, in vivo, or ex vivo. In vitro application of the fusion agents can be useful, for example, in basic scientific studies of immune mechanisms or for production of activated T cells for use in either studies on T cell function or, for example, passive immunotherapy.

In the in vitro methods of the invention, T cells (CD4+ and/or CD8+) obtained from a mammalian subject are cultured with a fusion agent of the invention and antigen presenting cells (APC), preferably, but not necessarily, obtained from the same individual as the T cells. Where the APC are obtained from a different individual, the donor of the T cells and the donor of the APC will preferably express at least one major histocompatibility complex (MHC) molecule (e.g., a MHC class I molecule) in common. APC can be essentially any MHC molecule-expressing cell. Where it is desired to elicit a MHC class I restricted immune response, the APC will express MHC class I molecules (and optionally MHC class II molecules) and where it is desired to elicit an MHC class II restricted immune response, the APC will express MHC class II molecules (and optionally MHC class I molecules). The APC will optimally also express one or more co-stimulatory molecules, e.g., the B7 family of molecules. Thus APC can be, for example, interdigitating dendritic cells (DC), macrophages, monocytes, B cells, or cell lines (clonal or non-clonal) derived from any of these cells. They can also be any cell type (e.g., fibroblasts) transfected or transduced with and expressing a polynucleotide encoding an appropriate MHC molecule. Such cultures can also be supplemented with one or more cytokines or growth factors such as, without limitation, IL-1, IL-2, IL-3, IL-4, IL-6, IL-7, IL-12, IL-13, IL-15, IFN-γ, tumor necrosis factor-α (TNF-α), granulocyte macrophage colony-stimulating factor (GM-CSF), or granulocyte-colony stimulating factor (G-CSF). The cultures can be "restimulated" as often as necessary with either the fusion agent or a peptide epitope component of the fusion agent not linked to the other components of the fusion agent. The cultures can also be monitored at various times to ascertain whether the desired level of immune reactivity (e.g., CTL activity) has been attained.

The fusion agents of the invention are generally useful for generating immune responses and as prophylactic vaccines or immune response-stimulating therapeutics. Thus, they can be used, for example, as vaccines or therapeutic agents against infectious diseases due to any of the pathogens listed herein. Due to their potent CTL activating potential, the fusion agents can be especially useful in the prevention and/or therapy of diseases involving intracellular microorganisms, e.g., viruses such as influenza virus or HIV, intracellular bacteria such *M. tuberculosis*, and intracellular protozoans such as *P. falciparum* or any of the others recited above. In addition, the fusion agents can be useful therapeutics for cancer (e.g., any of those recited above); in cases where a subject is at relatively high risk for a cancer (e.g., lung cancer in a tobacco smoker or melanoma in a subject with multiple nevi), appropriate fusion agents can be used as vaccines. Moreover, as described above, the fusion agents (e.g., those containing APL) can also be useful in therapy or prophylaxis of autoimmune diseases.

As used herein, "prophylaxis" can mean complete prevention of the symptoms of a disease, a delay in onset of the symptoms of a disease, or a lessening in the severity of subsequently developed disease symptoms. As used herein, "therapy" can mean a complete abolishment of the symptoms of a disease or a decrease in the severity of the symptoms of the disease.

It is understood that, while the responses generated by the TA of the invention are preferably prophylactic and/or therapeutic, it is not absolutely required that they be. For example, the TA can be used in basic scientific studies on immune responses that are neither prophylactic nor therapeutic.

The methods of the invention can be applied to a wide range of species, e.g., humans, non-human primates (e.g., monkeys), horses, cattle, pigs, sheep, goats, dogs, cats, rabbits, guinea pigs, hamsters, rats, and mice.

In Vivo Approaches

In one in vivo approach, the fusion agent itself is administered to the subject. Generally, the fusion agents of the invention will be suspended in a pharmaceutically-acceptable carrier (e.g., physiological saline) and administered orally or transdermally or injected (or infused) intravenously, subcutaneously, intramuscularly, intraperitoneally, intrarectally, intravaginally, intranasally, intragastrically, intratracheally, or intrapulmonarily. They can be delivered directly to an appropriate lymphoid tissue (e.g. spleen, lymph node, or mucosal-associated lymphoid tissue (MALT)). The dosage required depends on the route of administration, the nature of the formulation, the nature of the patient's illness, the subject's size, weight, surface area, age, and sex, other drugs being administered, and the judgment of the attending physician. Suitable dosages are in the range of 0.001-10.0 mg/kg. Wide variations in the needed dosage are to be expected in view of the variety of fusion agents available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding a fusion agent of interest can be delivered to an appropriate cell of the animal. Expression of the coding sequence will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med.* 73, 479]. Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), *Mol. Cell. Biol.* 12, 1043-1053; Todd et al. (1993), *J. Exp. Med.* 177, 1663-1674; Penix et al. (1993), *J. Exp. Med.* 178, 1483-1496]. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the fusion protein of interest with an initiator methionine and optionally a targeting sequence is operatively linked to a promoter or enhancer-promoter combination. Promoters and enhancers are described above.

Polynucleotides can be administered in a pharmaceutically acceptable carrier. Pharmaceutically acceptable carriers are biologically compatible vehicles which are suitable for administration to a human or other mammalian subject, e.g., physiological saline. A therapeutically effective amount is an amount of the polynucleotide which is capable of producing a medically desirable result (e.g., a T cell response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Ex Vivo Approaches

In one ex vivo approach, lymphoid cells, including T cells (CD4+ and/or CD8+ T cells), are isolated from the subject and exposed to the fusion agent in vitro (see above). The lymphoid cells can be exposed once or multiply (e.g., 2, 3, 4, 6, 8, or 10 times). The level of immune activity (e.g., CTL activity) in the lymphoid cells can be tested after one or more exposures. Once the desired activity and level of that activity is attained, the cells are reintroduced into the subject via any of the routes listed herein. The therapeutic or prophylactic efficacy of this ex vivo approach is dependent on the ability of the ex vivo activated lymphocytes to either: (a) exert, directly or indirectly, a neutralizing or cytotoxic effect on, for example, infectious microorganisms, host cells infected with microorganisms, or tumor cells; or (b) abate or reduce a pathogenic autoimmune T cell response as, for example, in RA, MS, IDDM, SLE, or MG either by a suppressive or an immune deviating mechanism.

An alternative ex vivo strategy can involve transfecting or transducing cells obtained from the subject with a polynucleotide containing a fusion agent-encoding nucleotide sequence. The transfected or transduced cells are then returned to the subject. While such cells would preferably be lymphoid cells, they could also be any of a wide range of types including, without limitation, fibroblasts, bone marrow cells, macrophages, monocytes, dendritic cells, epithelial cells, endothelial cells, keratinocytes, or muscle cells in which they act as a source of the fusion protein for as long as they survive in the subject. In subjects with cancer, the cells can be cancer cells, e.g., their own cancer cells or cells of the same cancer type but from another individual, preferably an individual having one or more (e.g., one, two, three, four, five, or six) MHC molecules in common with the subject. The use of lymphoid cells would be particularly advantageous in that such cells would be expected to home to lymphoid tissue (e.g., lymph nodes or spleen) and thus the fusion agent would be produced in high concentration at the site where they exert their effect, i.e., activation of an immune response. By using this approach, as in the above-described in vivo approach using fusion agent-encoding polynucleotides, active in vivo immunization with the fusion agent is achieved. The same genetic constructs and signal sequences described for the in vivo approach can be used for this ex vivo strategy.

The ex vivo methods include the steps of harvesting cells from a subject, culturing the cells, transducing them with an expression vector, and maintaining the cells under conditions suitable for expression of the fusion agent. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the fusion agent or of a drug resistance gene. If desired, the cells can be treated with an agent (e.g., x- or γ-irradiation or mitomycin C) that inhibits cell proliferation; generally where the cells are cancer cells (particularly cancer cells from the subject or from an individual that is MHC identical to the subject) will be so treated. The cells are then injected or implanted into the patient.

These methods of the invention can be applied to any of the diseases and species listed here. Methods to test whether a fusion agent is therapeutic for or prophylactic against a particular disease are known in the art. Where a therapeutic effect is being tested, a test population displaying symptoms of the disease (e.g., cancer patients) is treated with a test fusion agent, using any of the above described strategies. A control population, also displaying symptoms of the disease, is treated, using the same methodology, with a placebo. Disappearance or a decrease of the disease symptoms in the test subjects would indicate that the fusion agent was an effective therapeutic agent.

By applying the same strategies to subjects prior to onset of disease symptoms (e.g., presymptomatic subjects considered to likely candidates for SLE development or experimental animals in which an appropriate disease spontaneously arises, e.g., NZB mice, or can be deliberately induced, e.g., multiple murine cancers), fusion agents can be tested for efficacy as prophylactic agents, i.e., vaccines. In this situation, prevention of onset of disease symptoms is tested. Analogous strategies can be used to test for the efficacy of the fusion agents in the prophylaxis of a wide variety of infectious diseases, e.g., those involving any of the microorganisms listed above.

The following examples are meant to illustrate, not limit, the invention.

EXAMPLES

Example 1

Materials and Methods

Synthetic TA

Synthetic TA used in the experiments described below were synthetic peptides containing one or three minimal CTL epitopes.

In the TA containing one minimal CTL epitope, the CTL epitope was joined to the HIVtat protein transduction domain ("HPTD" having the amino acid sequence RKKRRQRRR (SEQ ID NO:1)) and there was a triple-alanine spacer between the minimal CTL epitope and the HPTD.

In the TA containing three minimal CTL epitopes, one of the epitopes was at the N-terminus of the polypeptide and was followed by the other two epitopes. The first and the second epitope and the second and the third epitope were separated by furin cleavable linkers having the amino acid sequence RVKR (SEQ ID NO:8) or a control VRVV (SEQ ID NO:9) amino acid sequence. The most C-terminal epitope had at its C-terminus three alanine residues followed by the above-described HPTD. All synthetic peptides were synthesized according to standard solid-phase synthesis methods using an Applied Biosystems (Foster City, Calif.) apparatus and were purified by high-performance liquid chromatography. The purity (>95%) and identity of peptides were determined by analytical high-performance liquid chromatography and mass spectrometry analysis. Peptides were dissolved at a concentration of 10 mg/ml in dimethyl sulfoxide(DMSO) containing 0.1% trifluoroacetyl or trifluoro-acetic acid and stored in small volumes at −20° C.

Recombinant TA

A recombinantly derived TA containing the melanoma gp100 epitope IMDQVPFSV (SEQ ID NO:10), linked to the Antennapedia homeodomain (AntpHD) translocating sequence RQIKIWFPNRRMKWKK (SEQ ID NO:2) was designed using an approach similar to that described by Shutze-Redelmeier et al. [(1996) J Immunol 157:650]. The CTL epitope was flanked with influenza NP amino acid sequences at the N-terminus (AEIDL) (SEQ ID NO:11) and the C-terminus (LRTED) (SEQ ID NO:12) to facilitate the correct processing. In order to produce the final product having the amino acid sequence (RQIKIWFPNRRMKWK-KAEIDLIMDQVPFSVLRTED) (SEQ ID NO: 13), two synthetic oligodeoxynucleotide (ODN) primers were prepared:

Primer A:
(SEQ ID NO: 14)
GACGACGACAAGATGCGTCAGATCAAGATCTGGTTCCCGAACCGTCGT
ATGAAGTGGAAGAAGGCAGAGATCGACCTG Primer B:
(SEQ ID NO: 15)
GAGGAGAAGCCCGGTCTAGTCTTCGGTACGCAGTACAGAGAACGGTAC
CTGGTCCATGATCAGGTCGATCTCTGCC These ODN are complementary in an overlap region of 16 bases at their 3' ends. Mixing equal molar concentrations of the ODN in the presence of Klenow Fragment DNA Polymerase (Boehringer Mannheim, Indianapolis, Ind.), the two primers annealed at their respective 3' ends and provided suitable priming sites and templates for a fill-in polymerase reaction to generate a 137 bp double strand DNA fragment. This fragment was purified and inserted into the EK/LTC 34 expression vector (Novagen, Madison, Wis.). Briefly, following the manufacturer's directions, the ends of the DNA fragment were digested by the exonuclease function of T4 polymerase in the presence of dATP to form compatible single strand cohesive ends complementary to the ek/lic expression vector's insertion site. By allowing the digested DNA fragment to anneal to the supplied linearized vector and quickly transforming into BL21competent E. coli cells, the insert and vector were ligated by the host cells replication and repair enzymes. Transformants were grown on selective media containing Kanamicin. The positively selected tranformants were then grown overnight in LB broth and plasmid DNA was recovered by a plasmid mini prep (Qiagen, Valencia, Calif.). Vector and insert sequencing confirmed that the correct construct had been made and was inserted in the frame. The plasmid was re-transformed into BL21 cells and induced in log phase by IPTG (isopropyl-é-D-thiogalactopyranoside) to produce a fusion protein containing the TA with amino acid sequence RQIKIWFPNRRMKWKKAEIDLIM-DQVPFSVLRTED (SEQ NO:13) fused to the cellulose binding (CB) protein. The TA peptide was cleaved from the CB protein by digestion with enterokinase (Novagen). The TA peptide was purified by HPLC on a C4 reverse phase column with an ACN (acetonitrile)/0.1% TFA (trifluoroacetic acid) gradient. Purity was determined by analytical HPLC and mass spectroscopy.

Cell Lines and CTL

The TAP-competent 221.A2 cell line, which was derived from a MHC class I deficient cell line transfected with HLA-A2 [Tsai et al. (1997) J. Immunol. 158:1796], and the TAP-deficient T2 human cell line [Salter et al. (1986) EMBO J. 5:943] were used as targets in cytotoxicity assays with the cells of HLA-A2-restricted human cytotoxic T lymphocyte (CTL) lines as effector cells. The TAP-competent EL-4 mouse cell line (H-$2^b$) and TAP-deficient T2 cells transfected with the mouse H-$2K^b$ alloantigen (T2/$K^b$) were used as APC for studies using the immunodominant H-$2K^b$-restricted CTL epitope from ovalbumin (OVA257, amino acid sequence SIINFEKL; SEQ ID NO:15). A transfected mouse L-cell line expressing the H-$2K^b$ antigen L-$K^b$ (provided by L. Pease, Mayo Clinic, Rochester, Minn.) was also used as a source of APC to study the presentation of the OVA$_{257}$ CTL epitope. The RMA-S cell line was used as a target cell in studies to test for the ability of a 3 peptide epitope TA to sensitize target cells for CTL-mediated lysis and to activate peptide-specific CTL responses in vivo. All cell lines were maintained in complete RPMI tissue culture medium (RPMI1640 supplemented with 10% (v/v) fetal bovine serum (FBS), L-glutamine, non-essential amino acids, sodium pyruvate, gentamycin and, when required, a selection drug). Human HLA-A2-restricted CTL lines, which recognize the IMIGVLVGV (SEQ ID NO:16) epitope from carcinoembryonic antigen (CEA) or the IMDQVPFSV (SEQ ID NO:10) melanoma CTL epitope from gp 100 were prepared and maintained in tissue culture as described. CTL specific for OVA$_{257}$, a peptide epitope (2C) derived from a mitochondrial protein, or a peptide epitope (LCMV) derived from a lymphocytic choriomeningitis virus protein were obtained by culturing splenocytes harvested from OT-1 T cell receptor (TCR) (H2$K^b$ restricted and specific for OVA$_{257}$) transgenic mice, TCR transgenic mice having transgenes encoding a TCR restricted by H-$2K^b$ and specific for the 2C peptide epitope, or TCR transgenic mice having transgenes encoding a TCR restricted by H-$2D^b$ and specific for the LCMV peptide epitope with either Concanavalin A (ConA) or with irradiated peptide-pulsed APC for 7 days. All culture materials were purchased from Life Technologies Inc. (Rockville, Md.).

Antibodies and Reagents

The 25D1.16 monoclonal antibody, specific for the $OVA_{257}/H-2K^b$ peptide-MHC class I molecular complex was produced from supernatants of hybridoma cells kindly provided by R. Germain (NCI, NIH). Polyclonal antibody (TGN38, specific for a trans-Golgi marker) and polyclonal antibody specific for calreticulin (an ER marker) were kindly provided by Dr. Mark McNiven (Mayo Clinic, Rochester, Minn.). Fluorescein isothiocyanate (FITC) conjugated goat antibody specific for mouse IgG (FITC anti-mIgG) (secondary antibody for detection of bound 25D1.16), Texas red conjugated goat antibody specific for rabbit IgG (TR anti-rIgG) (secondary antibody for detection of bound TGN38 or antibody specific for calreticulin), and Prolong Antifade Kit were purchased from Molecular Probes (Eugene, Oreg.). Protease inhibitors, lactacystin, pepstatin-A and decRVKR-CMK were purchased from BACHEM Bioscience Inc. (King of Prussia, Pa.), dissolved in DMSO, and stored in aliquots at $-20°$ C. Brefeldin-A (BFA) was purchased from the Sigma Chemical Co. (Saint Louis, Mo.).

Cytotoxicity Assays

In some experiments, the processing and presentation of peptides were determined in standard 4-6 h $^{51}Cr$ release cytotoxicity assays mediated by antigen-specific CTL. Peptide- or TA-pulsed targets were prepared by incubating cells (221.A2, T2, EL-4, T2/$K^b$, or RMA-S) with a predetermined concentration of TA or peptide epitope at 37° C. overnight. The cells were then washed and labeled with 300 µCi $^{51}Cr$ sodium chromate (Amersham Pharmacia Biotech, Piscataway, N.J.) for 1~2 hours at 37° C. Various numbers of effector CTL were mixed with $2\times10^4$ labeled targets in 96-round bottomed well plates in a final volume of 0.2 ml of complete medium. After 4-6 hour incubation at 37 C.°, 30 µl of supernatant were collected from each well and percentage of specific lysis was determined according to the formula: [(cpm of the test sample−cpm of spontaneous release)/(cpm of maximal release−cpm of spontaneous release)]×100, where "cpm of spontaneous release" are the cpm detected in supernatants from wells containing labeled target cells and no effector cells and "cpm of maximal release" are the cpm detected in supernatants from wells containing target cells and 0.1% Triton X-100 (detergent). The inhibitory effect of BFA was determined by pre-incubating the target cells with 1 µg/ml BFA for 1 hour before peptide pulsing and during peptide incubation and performing the cytotoxicity assay in the presence of 0.5 µg/ml BFA.

Flow Cytometry

The effects of protease inhibitors on antigen processing and presentation were evaluated by analysis of 25D1.16 staining on different antigen-pulsed EL-4 or T2/$K^b$ cells using flow cytometric analysis. In brief, EL-4 or T2/$K^b$ cells were washed twice with serum-free AIM-V medium (Life Technologies, Rockville, Md.), pre-treated with protease inhibitors (10 µM lactacystin, 100 µM pepstatin or 60 µM decRVKR-CMK) for 30 minutes and then pulsed with equimolar concentrations of different (as indicated) peptides at 37° C. overnight with the continuous presence of the corresponding protease inhibitors. The serum-free AIM-V medium was used in order to exclude the potential involvement of serum proteases during the peptide-pulsing process.

After washing the cells twice with FACS buffer (PBS (phosphate buffered saline) supplemented with 2% FBS and 0.2% sodium azide), peptide-loaded APC were stained with 25D1.16 antibody followed by FITC anti-mIgG for flow analysis. Untreated EL-4 and T2/$K^b$ cells were pulsed with peptides and stained as controls.

Immunofluorescence and Confocal Microscopy

T2/$K^b$ or L-$K^b$ cells were cultured overnight on poly-lysine treated glass coverslips. The culture medium was discarded, and the cells were gently washed with PBS. The cells were pre-incubated with serum-free AIM-V medium at 37° C. for 30 minutes and then incubated with peptide/TA solutions at the indicated concentrations for 12 hour at 37° C. After peptide loading, the cells were washed and fixed with 2% formaldehyde for 20 minutes at room temperature. For indirect immunofluorescence, fixed cell monolayers were permeabilized with 0.2% Triton X100 in PBS and incubated with PBS containing 5% goat serum to block non-specific protein binding sites. The cells were double-labeled with mouse monoclonal antibody 25D1.16 specific to $OVA_{257}/H-2K^b$ complex and rabbit polyclonal antibody TGN38 (TGN marker) or rabbit anti-calreticulin (ER marker), followed by 1 hour staining with FITC anti-mIgG and TR anti-rIgG as secondary antibodies. After washing, the coverslips were mounted for observation on glass slides using the Prolong Antifade Kit. The stained cells were examined and photographed with a Leica TCS-SL confocal laser-scanning microscope (Bensheim, Germany).

Example 2

Trojan Antigens (TA) Sensitize TAP-Deficient as Well as TAP-Functional Targets

A TA composed of a HLA-A2-restricted minimal CTL epitope ($CEA_{691}$) from carcinoembryonic antigen (CEA) linked via its carboxyl terminal end to the active portion of the membrane-translocating region of HIVtat ($CEA_{691}$-HIVtat; SEQ ID NO:17) (Table 2) and the minimal CTL epitope $CEA_{691}$ alone (i.e., without the membrane translocating region of HIVtat) were compared for their ability to sensitize HLA-A2$^+$ target cells for lysis by cells of a human CTL clone that recognize $CEA_{691}$ bound to a HLA-A2 molecule. Peptide $CEA_{691}$ would be predicted to bind directly to surface HLA-A2 molecules that are temporarily empty and/or to surface HLA-A2 molecules bearing low affinity binding ligands by the displacement of these peptides. It seemed probable, on the other hand, that $CEA_{691}$-HIVtat would be less efficient at sensitizing TAP-deficient target cells than $CEA_{691}$ both because peptide $CEA_{691}$-HIVtat would likely not bind to surface HLA-A2 molecules and it would need to enter the MHC class I processing pathway involving at least some proteolysis in the cytoplasm followed by transport of peptides into the ER by TAP. Surprisingly, when $CEA_{691}$-HIVtat and $CEA_{691}$ were tested for their ability to sensitize target cells for CTL lysis, the two peptides had similar, if not identical, activities on TAP-competent (FIG. 1A) and TAP-deficient (FIG. 1B) target cells.

TABLE 2

List of CTL Peptide Epitopes and TA

| Peptide epitope/TA | Amino Acid Sequence | SEQ ID NO: |
|---|---|---|
| $CEA_{691}$ | IMIGVLVGV | 16 |
| $CEA_{691}$-HIVtat | IMIGVLVGVAAARKKRRQRRR | 17 |
| HIVtat-$CEA_{691}$ | RKKRRQRRRAAAIMIGVLVGV | 23 |
| $CEA_{691}$-KKK | IMIGVLVGVKKK | 20 |
| $CEA_{691}$-RRR | IMIGVLVGVRRR | 21 |
| $CEA_{691}$-RKK | IMIGVLVGVRKK | 22 |
| $OVA_{257}$ | SIINFEKL | 15 |
| $OVA_{257}$-HIVtat | SIINFEKLAAARKKRRQRRR | 24 |
| HIVtat-$OVA_{257}$ | RKKRRQRRRAAASIINFEKL | 25 |
| $gp100_{209}$ | IMDQVPSFV | 10 |
| AntpHD-$gp100_{209}$ | RQIKIWFPNRRMKWKKAEIDLIMDQVPFSVLRTED | 13 |
| $HBc_{18-27}$ | FLPSDYFPSV | 18 |
| TA3-A | IKAVYNFATCGRVKRSIYRYYGLRVKRSIINFEKLAAARKKRRQRRR | 28 |
| TA3-B | SIINFEKLRVKRIKAVYNFATCGRVKRSIYRYYGLAAARKKRRQRRR | 30 |
| TA3-C | IKAVYNFATCGVRVVSIYRYYGLRVVSIINFEKLAAARKKRRQRRR | 29 |
| TA3-D | RKKRRQRRRIKAVYNFATCGRVKRSIINFEKLRVKRSIYRYYGL | 32 |
| 2C | SIYRYYGL | 27 |
| LCMV | IKAVYNFATCG | 31 |
| E1A | SGPSNTPPEI | 33 |
| P1A | LPYLGWLVF | 34 |
| TRP-2 | SVYDEFFVWL | 35 |
| TA-5 | RKKRRQRRRAAASVYDEFFVWLKVKRLPYLGWLVFKVKRSGPSNTPPEI | 36 |
| TA-6 | RKKRRQRRRAAASVYDEFFVWLVRVVLPYLGWLVFVRVVSGPSNTPPEI | 37 |

Underlined residues correspond to the minimal CTL peptide epitope

Example 3

Target Cell Sensitization by TA Requires Intracellular Loading

The ability of $CEA_{691}$-HIVtat to sensitize TAP-deficient T2 cells for CTL lysis could have been due to the ability of this peptide to translocate across intracellular membranes utilizing the HIVtat carrier into the ER where it would be processed into the optimal CTL epitope. Another possiblibility was that $CEA_{691}$-HIVtat was degraded extracellularly by serum or cell-derived proteases; in this way the $CEA_{691}$ minimal epitope was generated and it then bound to surface HLA-A2 molecules. To explore the latter possibility the capacity of an irrelevant HLA-A2-binding peptide $HBc_{18-27}$ (SEQ ID NO:18; Table 2), to block the binding to surface HLA-A2 molecules of peptide $CEA_{691}$ per se or as a putative product of $CEA_{691}$-HIVtat proteolysis was tested. As shown in FIG. 2A, peptide $HBc_{18-27}$ was efficient at inhibiting the sensitization of target cells for CTL lysis by peptide $CEA_{691}$ but not sensitization by the $CEA_{691}$-HIVtat polypeptide. This result indicated that $CEA_{691}$-HIVtat was not cleaved by culture medium serum or cell-derived proteases. Another approach to evaluate whether peptide $CEA_{691}$-HIVtat is required to penetrate the cell in order to generate the CTL epitope involved treating the peptide with trypsin (which cleaves at the carboxyl end of R or K residues) and thus destroys (or decreases) the carrier function of HIVtat. The products of trypsin digest, for example IMIGVLVGVAAAR (SEQ ID NO:19), would be predicted to lose their membrane translocating activity but to retain susceptibility to proteolysis by a putative extracellular protease. The data presented in FIG. 2B indicate that after extensive treatment with trypsin, the $CEA_{691}$-HIVtat polypeptide lost most of its activity with respect to sensitizing target cells for CTL lysis. As expected, trypsin-treatment of $CEA_{691}$ did not modify this peptide's sensitizing activity. Thus it seemed likely that in order to sensitize target cells for CTL-mediated lysis, it was necessary for $CEA_{691}$-HIVtat to penetrate the cells.

In order to further eliminate the possibility that peptide $CEA_{691}$-HIVtat could be processed extracellularly by a carboxypeptidase, three additional peptides containing the $CEA_{691}$ CTL epitope were prepared. These peptides were elongated by three positive charged amino acids ($CEA_{691}$-KKK (SEQ ID NO:20), $CEA_{691}$-RRR (SEQ ID NO:21) and $CEA_{691}$-RKK (SEQ ID NO:22)) at their carboxy-termini (Table 2). In addition, another TA bearing the $CEA_{691}$ epitope was prepared. In this TA (HIVtat-$CEA_{691}$) (SEQ ID NO:23; Table 2) the CTL epitope was placed at the carboxyl terminus end of the polypeptide. If extracellular carboxypeptidases were involved, this HIVtat-$CEA_{691}$ would likely not be active. The results shown in FIG. 2C demonstrate that $CEA_{691}$-HIVtat and HIVtat-$CEA_{691}$ displayed similar capacities to sensitize targets for CTL lysis. In contrast, none of peptides $CEA_{691}$-KKK, $CEA_{691}$-RRR or $CEA_{691}$-RKK were able to sensitize the target cells for lysis. In summary, these results provide strong evidence that TA containing the HIVtat carrier sequence are processed intracellularly and that CTL epitopes can be generated in a TAP-independent manner. In addition, the data also indicate that a strong positive charge (KKK, RRR or RKK) at one end of the peptide is alone not sufficient to allow these peptides to translocate into the cells to generate CTL epitopes and that the entire TA membrane translocating portion is required for translocation.

Example 4

Antigen Processing and Trimming of TA

In order to extend these observations to another CTL epitope and to a different TD, a TA polypeptide containing the HLA-A2 restricted melanoma CTL epitope $gp100_{209}$ (SEQ ID NO:10) was attached to the active carrier portion of AntpHD (SEQ ID NO:2). This TA was prepared using recombinant methods. The resulting TA (AntpHD-$gp100_{209}$; (SEQ ID NO:13; Table 2) also contained flanking sequences of influenza NP to facilitate antigen processing. Both TAP-competent (FIG. 3A), and TAP-deficient targets (FIG. 3B) were efficiently sensitized by peptide AntpHD-$gp100_{209}$ for lysis by a $gp100_{209}$-specific CTL clone. These results show that different types of TA are effective in generating CTL epitopes in a TAP-independent manner.

As suggested above, the capacity of TA to generate peptide/MHC complexes (which are recognized by CTL) in a TAP-independent manner may be via the delivery of epitopes directly into the ER. Once in the ER the TA could be "trimmed" allowing the formation of peptide/MHC complexes that would be exported via the Golgi to the cell surface. Such a process would be predicted to be blocked by brefeldin-A (BFA), which inhibits the transport of products from the ER to the Golgi [Yewdell et al. (1989) Science 244:1072]. The data in FIG. 4 show that BFA was indeed effective in blocking the sensitization of TAP-deficient T2 cells by HIVtat-$CEA_{691}$ and AntpHD-$gp100_{209}$ but did not block sensitization by the minimal epitopes $CEA_{691}$ and $gp100_{209}$. Less inhibition was observed at high concentrations of TA; thus, TA may deliver CTL epitopes to cellular compartments other than the ER where MHC/peptide complexes can be formed. Alternatively, the transport of the TA peptide to the Golgi from the ER at high concentrations might not be inhibitable by BFA in this system.

Example 5

Intracellular Localization of TA and Corresponding Peptide/MHC Complexes

The above experiments indicate that TA likely have the property of penetrating intracellular compartments where they can be processed to generate peptide/MHC complexes corresponding to CTL epitopes. En order to assess the formation of these complexes intracellularly, TA containing the immunodominant mouse H-$2K^b$-restricted CTL epitope, $OVA_{257}$ (SEQ ID NO:15; Table 2) (derived from the ovalbumin protein) were prepared. $OVA_{257}$ was linked to the HIVtat carrier, either at the carboxyl or amino terminal end, creating the $OVA_{257}$-HIVtat (SEQ ID NO:24) or HIVtat-$OVA_{257}$ (SEQ ID NO:25) polypeptides, respectively (Table 2). Polypeptides $OVA_{257}$-HIVtat and HIVtat-$OVA_{257}$ were first compared with the $OVA_{257}$ for their capacity to sensitize TAP-competent and TAP-deficient target cells for CTL lysis. The peptide titration curves presented in FIG. 5 indicate that both of these TA were effective, and actually 10-1000 fold more potent than $OVA_{257}$, in sensitizing both cell-types for lysis by antigen-specific CTL.

Utilizing the monoclonal antibody 25D1.16 that specifically reacts with H-$2K^b$/$OVA_{257}$ complexes and confocal microscopy, the formation and presence of this CTL epitope in permeabilized TAP-competent and TAP-deficient cells expressing H-$2K^b$ was evaluated. These studies showed that H-$2K^b$/$OVA_{257}$ complexes were abundant in TAP-competent cells that had been incubated with either HIVtat-$OVA_{257}$ or $OVA_{257}$. These cells were also stained with an antibody specific for calreticulin which is localized within the ER. After superimposing the corresponding images, it was apparent that abundant H-$2K^b$/$OVA_{257}$ complexes were present within the ER in the cells that were incubated with peptide HIVtat-$OVA_{257}$, but not in those cells incubated with $OVA_{257}$. Experiments using TAP-deficient cells and experiments using $OVA_{257}$-HIVtat gave similar results.

An antibody specific for trans-Golgi network (TGN38) was used to test whether H-$2K^b$/$OVA_{257}$ complexes could also be detected in the trans-Golgi network of cells incubated with TA peptides. High amounts of intracellular H-$2K^b$/$OVA_{257}$ complexes were seen in TAP-deficient cells (T2/$K^b$) that were incubated with $OVA_{257}$-HIVtat. In these cells, antibody TGN38 stained brightly a structure corresponding to the trans-Golgi. By superimposing these images, it is evident that the majority of the H-$2K^b$/$OVA_{257}$ complexes localized within the trans-Golgi. On the other hand no localization to the trans-Golgi of H-$2K^b$/$OVA_{257}$ complexes could be observed in T2/$K^b$ cells that were treated with peptide $OVA_{257}$. Furthermore, it was apparent that in cells sensitized with $OVA_{257}$, most of the H-$2K^b$/$OVA_{257}$ complexes were on the cell-surface. These observations reinforce the findings that TA peptides need to penetrate cells in order to create MHC class I/peptide complexes. In addition, these complexes are observed in both the ER and trans-Golgi, even in TAP-deficient cells.

Example 6

Effects of Protease Inhibitors on the Processing and Presentation of TA

The data described above indicate that TA can be processed in various cellular compartments to produce small peptide epitopes that subsequently associate with MHC class I molecules and the resulting peptide-MHC class I complexes are then transported to the cell surface. Antigen processing could take place: (1) in the cytoplasm, via proteasomal degradation followed by TAP transport; (2) within the ER, where peptide trimming via an aminopeptidase could occur; (3) in the trans-Golgi, where processing of antigens through proteases such as furin can occur; and/or (4) in early endocytic compartments, where peptides that could either bind to recycling MHC class I molecules or leak into other compartments of the MHC class I pathway can be generated. Utilizing antibody 25D1.16, we studied the effects of various inhibitors of antigen processing in the formation of H-2K$^b$/OVA$_{257}$ surface complexes by peptides OVA$_{257}$-HIVtat and HIVtat-OVA$_{257}$. As shown in FIG. 6, inhibition of proteasome activity using lactacystin (10 µM, the highest concentration used without substantially compromising the viability of cells) did not have an effect on the amount of surface H-2K$^b$/OVA$_{257}$ complexes expressed on TAP-competent EL-4 cells (FIGS. 6A and 6B). Similarly, this proteasomal inhibitor did not have an appreciable effect on the surface expression of these complexes induced by peptide HIVtat-OVA$_{257}$ on TAP-deficient cells (FIG. 6D). Interestingly, lactacystin appeared to increase about 3-fold the level of peptide/MHC complexes resulting from the processing of the OVA$_{257}$-HIVtat polypeptide in TAP-deficient cells (FIG. 6C). These results suggest that much (at least) of the processing of these TA does not take place in the cytoplasm, even in TAP-competent cells.

The effect of the endosomal aspartyl-protease inhibitor pepstatin-A in the generation of H-2K$^b$/OVA$_{257}$ complexes on TAP-competent and TAP-deficient cells was studied. Interestingly, pepstatin-A increased by 3-5 fold the amounts of surface peptide/MHC class I complexes produced by OVA$_{257}$-HIVtat expressed on both TAP-competent and TAP-deficient cells (FIGS. 7A and 7C). On the other hand, pepstatin-A did not have an appreciable effect on the formation of H-2K$^b$/OVA$_{257}$ complexes by the HIVtat-OVA$_{257}$ polypeptides in both cell-types (FIGS. 7B and 7D). Similar results were obtained using other agents that inhibit endosomal and lysosomal degradation such as NH$_4$Cl and chloroquine. These findings indicate that TA are not significantly processed in the endocytic compartment to generate CTL epitopes.

The above results suggested that TA's are likely processed in the ER or in the trans-Golgi to effectively produce CTL epitopes. It has been shown that an ER-resident aminopeptidase is responsible for trimming peptides into their optimal size for MHC binding. On the other hand, there is no clear evidence of the existence of a carboxypeptidase-trimming enzyme in this compartment. Thus, TA containing the CTL epitope at the carboxyl-terminal end, but not those situated at the amino-terminal end, have been shown to generate CTL epitopes in the ER. These findings would help explain how HIVtat-OVA$_{257}$ may be processed into the OVA$_{257}$ CTL epitope once it translocates into the ER. However, it would be predicted that the OVA$_{257}$-HIVtat polypeptide would not effectively produce the OVA$_{257}$ CTL epitope in the ER, unless other proteolytic mechanisms besides the aminopeptidase are involved. Moreover, one would expect that the OVA$_{257}$ CTL epitope in OVA-1-HIVtat would be destroyed by the amionopeptidase.

It seemed possible that the TA could be processed in the trans-Golgi by the endopeptidase action of the furin family of enzymes which cut at the C-terminal side of dibasic amino acid recognition sequences. Thus, the furin inhibitor decRVKR-CMK (60 µM) was tested for its ability to block the formation of peptide/MHC class I surface complexes generated by TA. As shown in FIG. 8, decRVKR-CMK decreased by about 10-fold the expression of surface H-2K$^b$/OVA$_{257}$ complexes generated by OVA$_{257}$-HIVtat in both TAP-competent and TAP-deficient cells (FIGS. 8B and 8E). In contrast, no effect was observed in the formation of the peptide/MHC complexes induced by either HIVtat-OVA$_{257}$ (FIGS. 8C and 8F) or OVA$_{257}$ (FIGS. 8A and 8D) in both cell-types. These results indicate that furin (or a similar protease) is likely to play an important role in the processing of TA that bear the CTL epitope at the amino-terminus end, possibly by removing a portion of the carrier, which contains several furin motifs. Nevertheless, the smallest product of furin processing for this TA, SIINFEKLAAARK (SEQ ID NO:26), would still require additional processing in the ER or trans-Golgi, possibly by the action of a putative carboxypeptidase, in order to generate a peptide capable of binding to the H-2K$^b$ MHC class I molecule.

Example 7

Figure 9:
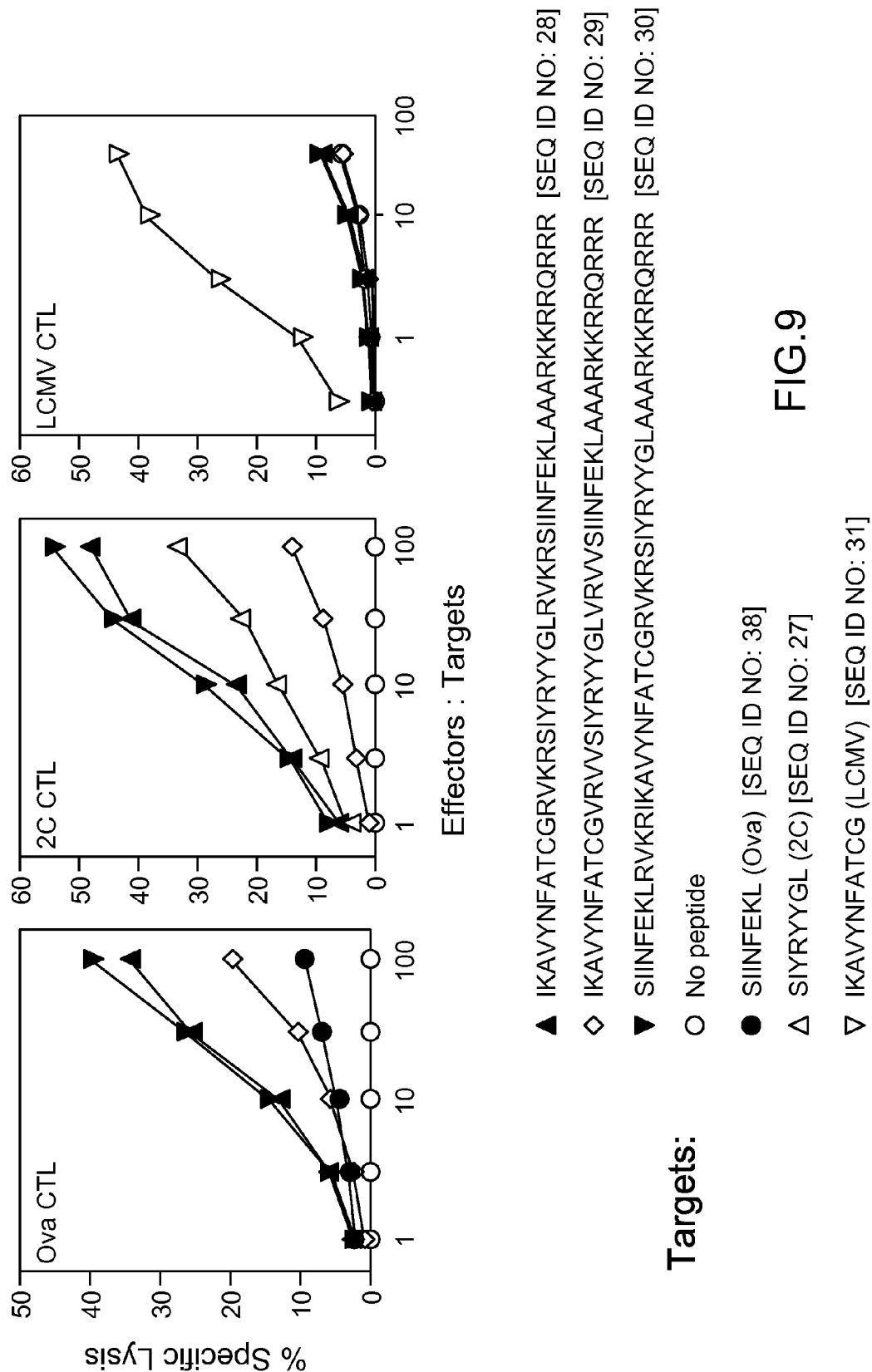
FIG. 9 is a set of three line graphs showing the cytotoxic activity ("% Specific Lysis") of CTL (at multiple effector to target ratios) specific for the $OVA_{257}$ peptide epitope (left panel), the 2C peptide epitope (middle panel), or an LCMV peptide epitope (right panel) against TAP-deficient RMA-S target cells that had been incubated overnight with 10 µM of either the $OVA_{257}$ peptide epitope (black circles), the 2C peptide epitope (white triangles), the LCMV peptide epitope (inverted white triangles), the TA TA3-A (black triangles), the TA TA3-B (inverted black triangles), the TA TA3-C (white diamonds), or medium with no peptide epitope or TA (white circles). The CTL were generated by Concanavalin A activation of T cells from transgenic mice expressing transgenes encoding TCR specific for the appropriate $H-2K^b$/peptide epitope complexes. Data shown are the means of triplicate values; standard deviations were in no case greater than 10% of the mean values.

Capacity of TA Containing Multiple CTL Epitopes to Sensitize Target Cells for CTL-Mediated Lysis TAP deficient RMA-S targets were incubated overnight with the peptides shown in FIG. 9 and they were then tested for their capacity to be killed by antigen-specific CTL generated by ConA activation of T cells from transgenic mice having transgenes encoding TCR specific for the relevant peptide epitopes presented by H-2 MHC class I molecules. CTL specific for the OVA$_{257}$ (FIG. 9, left panel) and 2C (FIG. 9, middle panel) peptide epitopes could effectively kill targets sensitized with two TA (TA3-A and TA3-B; SEQ ID NO:28 and SEQ ID NO:29, respectively; Table 2) containing CTL epitopes joined with furin sensitive linkers (RVKR). The Trojan antigen with non-furin linkers (VRVV) (TA3-C; SEQ ID NO:30; Table 2) was much less effective. In contrast, none of the TA were capable of sensitizing targets for lysis by the CTL specific for the LCMV peptide epitope (FIG. 9, right panel); only the short minimal epitope was effective.

Different results were obtained in an experiment that was similar to that shown in FIG. 9 except that the CTL were activated by stimulating the cells with the relevant peptide epitope rather than ConA. The capacity of several TA to sensitize target cells for CTL lysis was examined using RMA-S target cells that had been incubated overnight with the molecules shown in the figure legend. The following day the targets were tested for susceptibility to lysis by the appropriate peptide-specific CTL. The results show that CTL specific for all three peptide epitopes (FIG. 10, all three panels) could kill targets sensitized with the two TA containing CTL epitopes joined with furin sensitive linkers (SEQ ID NOS:28 and 29; Table 2) and the HIVtat carrier sequence at the C terminus. The cytotoxic activity of the LCMV-specific CTL, in contrast to the OVA$_{257}$- and 2C-specific CTL, was significantly lower on RMA-S target cells pulsed with any of the TA-containing furin linkers (FIG. 10C; "closed circles", "closed squares", and "closed triangles") than on RMA-S target cells pulsed with the LCMV peptide epitope per se ("open diamonds").

Figure 10:
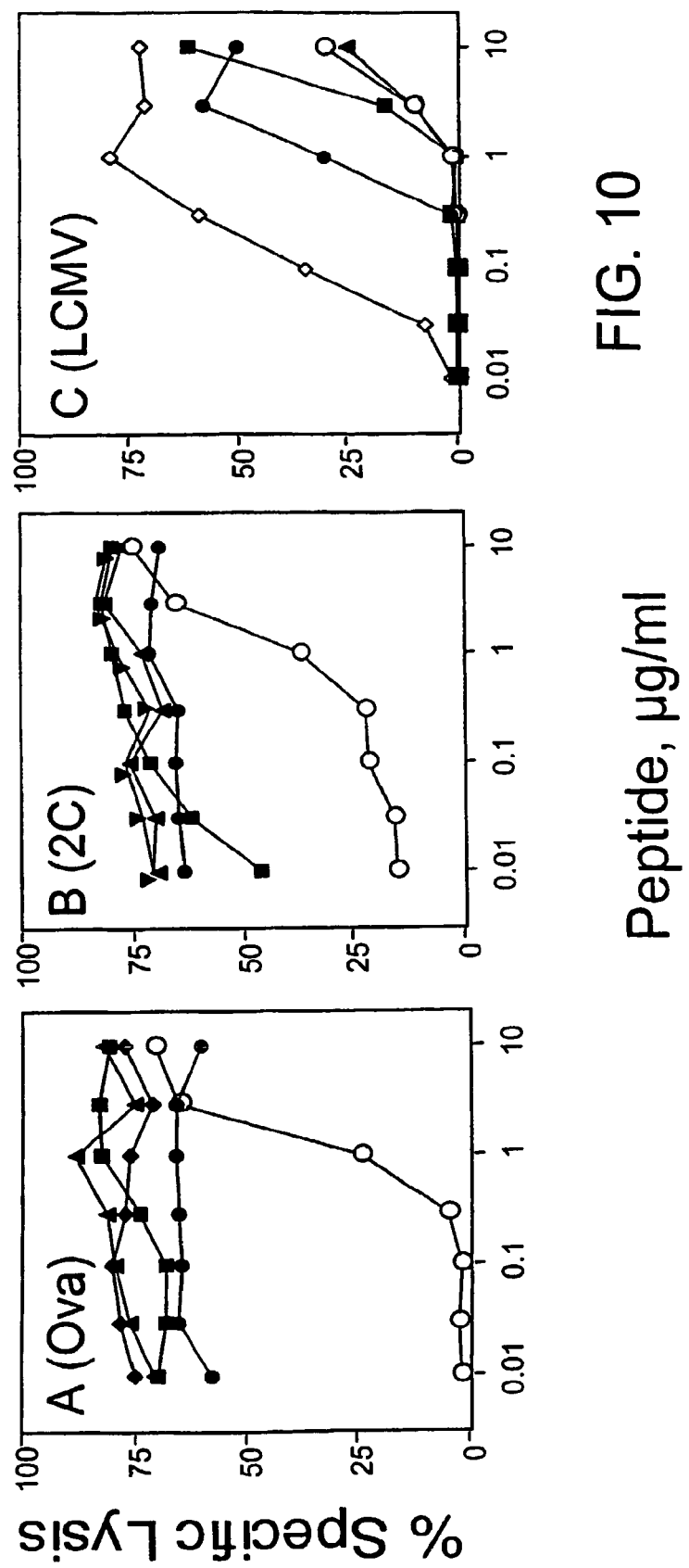
FIGS. 10A-C are three line graphs showing the cytotoxic activity ("% Specific Lysis") of CTL (at an effector to target cell ratio of 10:1) specific for the $OVA_{257}$ peptide epitope ("Ova"

The TA having non-furin linkers (TA3-C; Table 2) also sensitized the RMA-S targets for lysis (FIG. 10; data indicated by "open circles") but was at least 100-fold less effective than the corresponding TA containing furin-sensitive linkers (Table 2; TA3-A) (FIG. 10; data indicated by "closed circles"). These data suggest that other proteases in the ER or Golgi besides furin can process antigens.

A TA containing the HIVtat at the amino terminal end (TA3-D; Table 2) was also tested (white squares) for its ability to sensitize the RMA-S targets for lysis. This polypeptide was as effective as the others with the $OVA_{257}$- and 2C-specific CTL (FIG. 10, left and middle panels) but less effective with the LCMV-specific CTL (FIG. 10, right panel).

The relatively lower activity of the LCMV-specific CTL on TA-sensitized RMA-S target cells is likely due to the lower affinity of the LCMV-specific CTL for the relevant peptide-MHC class I molecular complex. This conclusion is suggested by the relatively high amount of the peptide epitope required to sensitize the RMA-S cells for lysis (FIG. 10C; "open diamonds").

Example 8

Capacity of TA Containing Multiple CTL Epitopes to Induce CTL Responses In Vivo

Figure 11A:
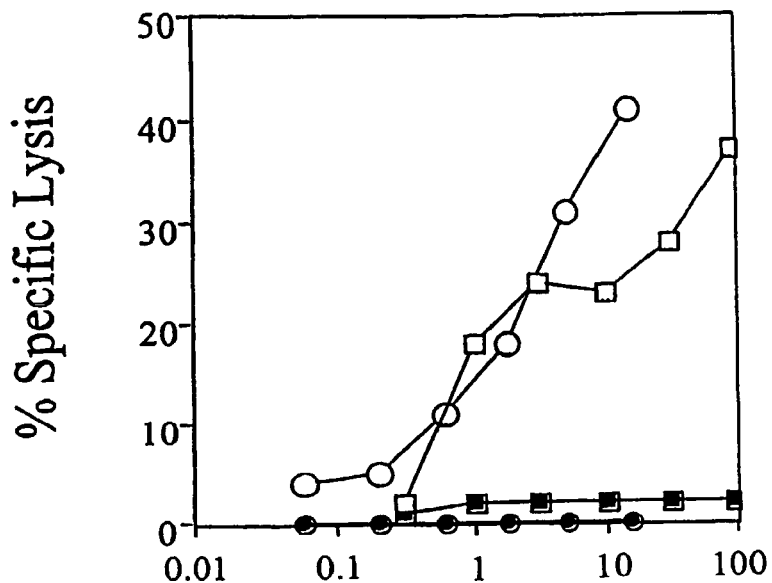
FIGS. 11A-11C are three line graphs showing the cytotoxic activity ("% Specific Lysis") of CTL (at multiple effector to target ratios) against TAP-deficient RMA-S target cells that had been incubated overnight with 10 µM of either the $OVA_{257}$ peptide epitope (FIG. 11A, white symbols), the 2C peptide epitope (FIG. 11B, white symbols), the LCMV peptide epitope (FIG. 11C, white symbols) or medium without a peptide epitope (FIGS. 11A-11C, black symbols). The CTL were activated by in vivo injection of C57BL/6 mice with either the TA TA3-A (circles) or a mixture of the $OVA_{257}$, the 2C, and the LCMV peptide epitopes (squares), followed by in vitro activation of spleen cells from the mice with either peptide $OVA_{257}$ peptide epitope (FIG. 11A), the 2C peptide epitope (FIG. 11B), the LCMV peptide epitope (FIG. 11C) or medium without a peptide epitope (FIGS. 11A-11C). Data shown are the means of triplicate values; standard deviations were in no case greater than 10% of the mean values.
Figure 11B:
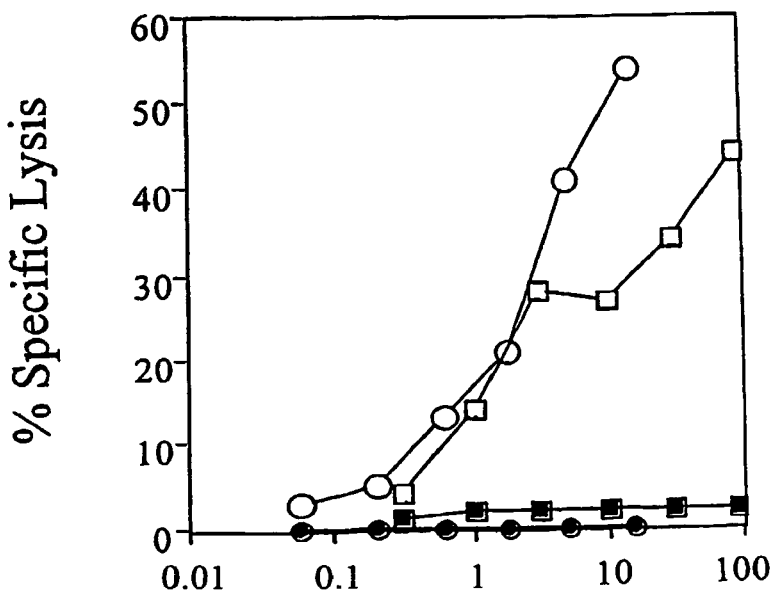
Figure 11C:
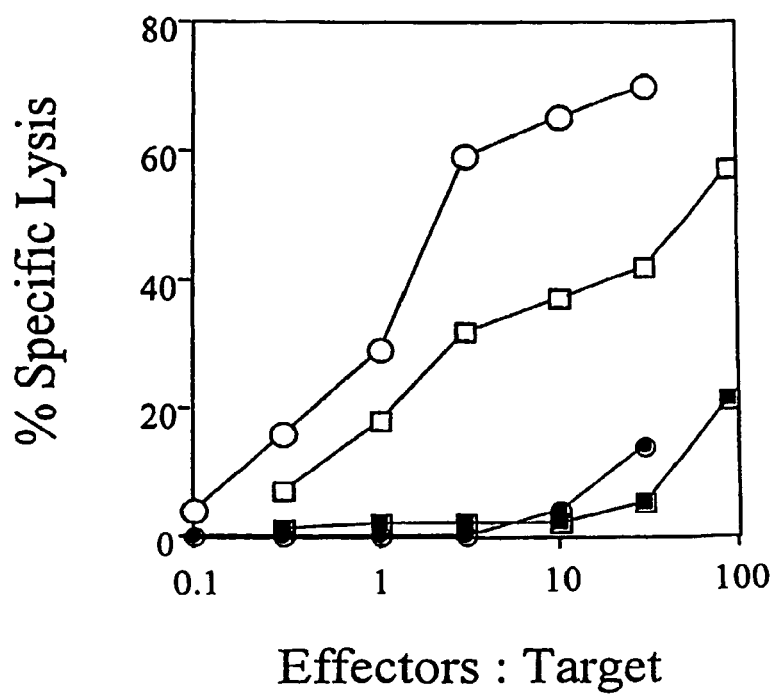

C57BL6 mice were vaccinated with a TA (TA3-A; Table 2) containing three CTL epitopes ($OVA_{257}$; 2C, and LCMV; Table 2) or with a mixture of the three relevant peptide epitopes per se ($OVA_{257}$+2C+LCMV). The mice received 9 daily injections of CpG adjuvant (100 ig in PBS) [Davila et al. (2000) J. Immunol. 165:539-547]. On the fifth day they were also injected with 40 µg of immunogen (40 ig of TA or a mixture containing 40 µg of each peptide epitope) emulsified in incomplete Freund's adjuvant (IFA). Ten days after the last injection the mice were sacrificed and their spleens were removed. Aliquots of the spleen cells were cultured with one of the three peptide epitopes (10 µg/ml) for 7 days in DMEM tissue culture medium containing 10% FBS. On day 7, the cell populations were harvested, washed, and their cytotoxic activities were measured in a 4 hr cytotoxicity assay using TAP-deficient RMA-S target that had been sensitized with the appropriate CTL peptide epitope (FIGS. 11A-11C). The results obtained with the mice immunized with the TA are shown with "circles". The results obtained with the mice immunized with the peptide mixture are shown with "squares". The white symbols show data obtained with targets pulsed with the relevant peptide and the black symbols show data obtained with the targets not exposed to peptide. FIG. 11A shows results obtained with the CTL cultures stimulated with the $OVA_{257}$ peptide. FIG. 11B from cultures stimulated with the 2C peptide and FIG. 11C with the LCMV peptide. These results demonstrate that the TA was at least as effective as the peptide mixture at inducing CTL responses by in vivo vaccination.

Figure 12:
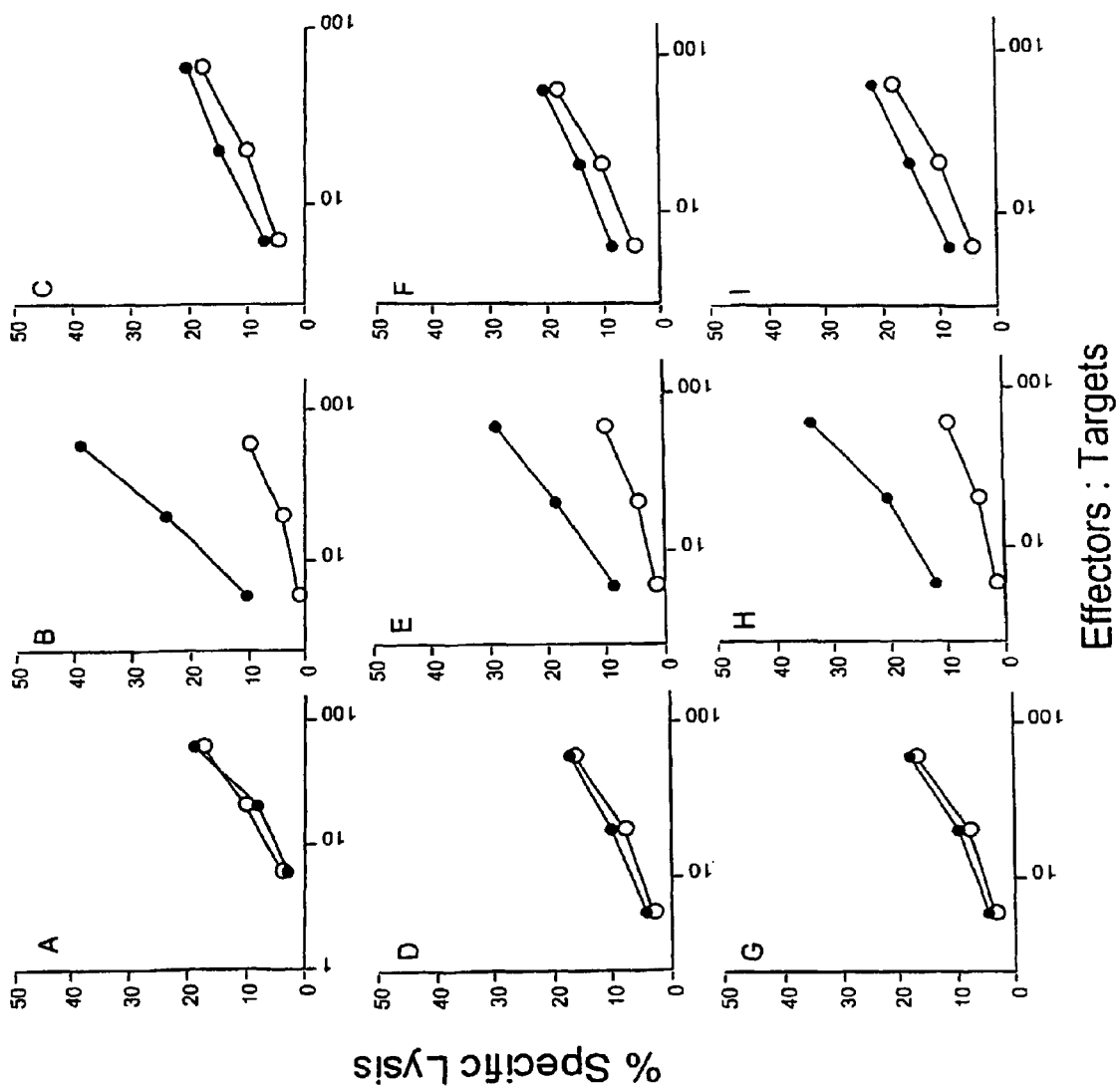
FIGS. 12A-I are nine line graphs showing the cytotoxic activity ("% Specific Lysis") of CTL (at three effector to target ratios) against TAP-deficient RMA-S target cells that had been incubated overnight with medium alone (FIGS. 12A-I; ("open circles")) or 10 µM of either the E1A peptide epitope (FIGS. 12A-C; "closed circles"), the P1A peptide epitope (FIGS. 12D-F; "closed circles"), or the TRP-2 peptide epitope (FIGS. 12G-I; "closed circles"). The CTL were activated by in vivo injection of C57BL/6 mice with either the TA TA5 (FIGS. 12B, E, and H), the TA TAG (FIGS. 12C, F, and I) or a mixture of the E1A, P1A, and TRP-2 peptide epitopes (FIGS. 12A, D, and G), followed by in vitro culture of spleen and lymph node cells from the mice with interleukin-2 for seven days. Data shown are the means of triplicate values; standard deviations were in no case greater than 10% of the mean values.

The above experiment was repeated with minor variations and using two multiple epitope TA containing three weakly immunogenic peptide epitopes linked by either furin-sensitive linkers (Table 2; TA6) or furin-insensitive linkers (Table 2; TA6). The three weakly immunogenic peptide epitopes were: (a) a peptide derived from the adenoviral E1A polypeptide (Table 2; E1A); (b) a peptide derived from a polypeptide expressed by murine P815 mastocytoma cells (Table 2; P1A); and (c) a peptide derived from tyrosinase-related protein 2 expressed by melanoma cells (Table 2; TRP2). The mice were immunized as described above except that 50 µg of each TA (or a mixture of each peptide epitope containing 50 µg of each) emulsified in IFA was used for immunization. Seven days after the immunization, the mice were sacrificed, their spleens and lymph nodes draining the site of immunization were removed, and cell suspensions were prepared from the spleens and lymph nodes pooled from each group of mice. Aliquots of each lymphoid cell preparation were cultured without antigen but with human IL-2 (150 U/ml) for 7 days. The cells were then harvested and tested for cytotoxic activity against either unpulsed RMA-S target cells (FIG. 12; "open circles") or RMA-S target cells pulsed with either the E1A peptide epitope (FIG. 12A-C), the P1A peptide epitope (FIGS. 12D-F) or the TRP-2 peptide epitope (FIGS. 12G-I) ("closed circles"). While no significant cytotoxic activity was seen on target cells pulsed with an appropriate peptide epitope (compared with unpulsed target cells) using effector cells generated by immunization of mice with either the pool of peptide epitopes (FIGS. 12A, D, and G) or TAG (FIGS. 12C, F, and I), significant peptide epitope-specific cytotoxic activity was detected with effector cells generated by immunization with TA5 (FIGS. 12B, E, and H). Thus, under circumstances in which a peptide epitope does not per se induce a detectable CTL response in vivo, immunization with a multi-epitope TA containing three such weakly immunogenic peptide epitopes induces significant CTL responses to all three peptide epitopes, provided that, in the TA, the peptide epitopes are linked by an appropriate proteolytic enzyme recognition site.

Example 9

Figure 13:
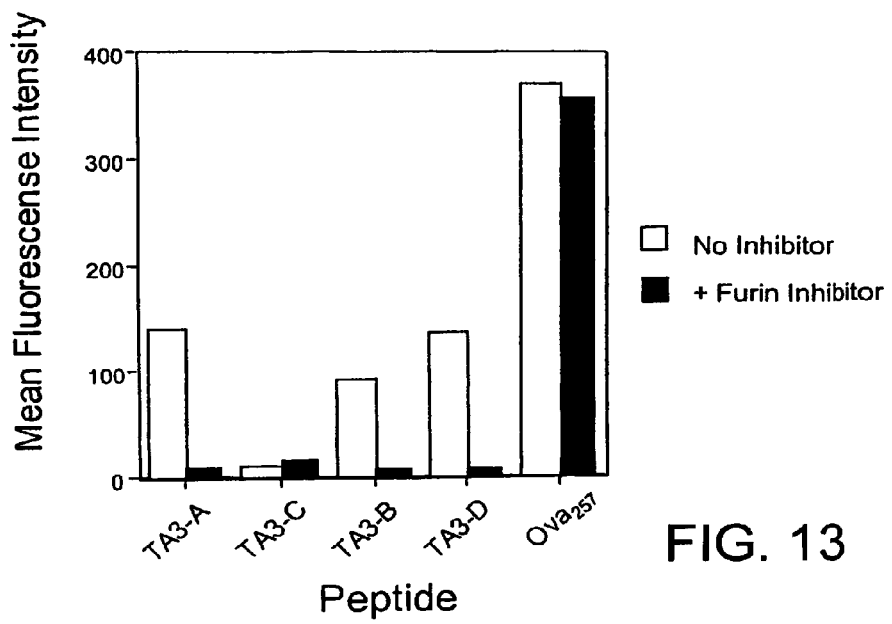
FIG. 13 is a bar graph showing the Mean Fluorescence Intensity obtained by fluorescence flow cytometry of RAM-S cells stained with the 25D1.16 antibody (specific for the $H-2K^b/OVA_{257}$ molecular complex) after incubation of the cells with the TA TA3-A, the TA TA3-B, the TA TA3-C, the TA TA3-D, or the $OVA_{257}$ peptide epitope, in the presence ("closed bars") and absence ("open bars") of the furin inhibitor decRVKR-CMK.

Effect of a Furin Inhibitor on the Processing and Presentation of TA Containing Multiple Peptide Epitopes Linked by Furin Sites Aliquots of RMA-S cells were cultured without or with the furin inhibitor decRVKR-CMK (60 µM) at 37° C. After one hour of culture, 4 multiple epitope-containing TA (TA3-A, TA3-B, TA3-C, and TA3-D) or $OVA_{257}$ were each added to separate cultures, which were then incubated for a further 18 hours. The cells were then harvested and the relative amounts of $H-2K^b/OVA_{257}$ complexes expressed on the surfaces of the cells were assessed by fluorescence flow cytometry using the 25D1.16 antibody (FIG. 13). Exposure of the cells to $OVA_{257}$ and all the TA, except that with the furin-insensitive linkers (TA3-B), resulted in detectable levels of cell-surface $H-2K^b/OVA_{257}$. Moreover, the presence of decRVKR-CMK in the cultures inhibited the cell-surface expression of $H-2K^b/OVA_{257}$ by induced by the TA but not by $OVA_{257}$. These findings underscore the importance of furin in processing of antigens to generate peptide epitopes that bind to MHC class I molecules and are then recognized by appropriate peptide epitope-specific CTL.

Example 10

Persistence of TA Peptide in Antigen Presenting Cells (APC)

Murine dendritic cells (DC) were prepared by culturing C57BL6 mouse ($H-2^b$) bone marrow macrophages in the presence of granulocyte macrophage colony stimulating factor (GM-CSF) and interleukin-4 (IL-4) by a method essentially the same as that described by Son et al. [(2002) J. Immunol. Meth. 262:145-157] except that non-adherent cells are removed from the cultures and discarded on day 2 of culture and no density gradient centrifugation step was used. Cells not adhering to the plastic tissue culture vessel at day 6 of culture were harvested and used as DC.

Figure 14:
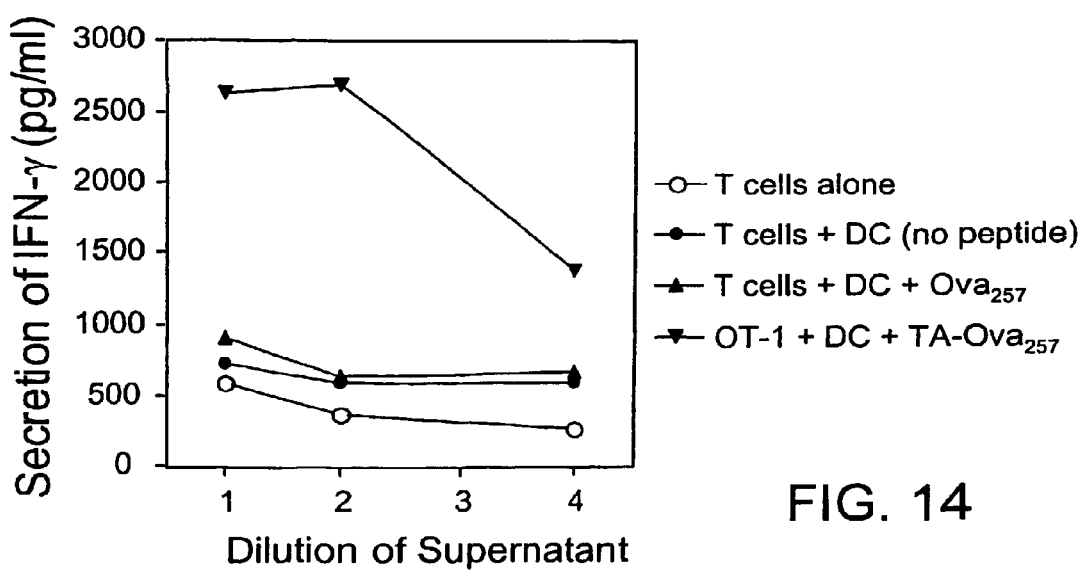
FIG. 14 is a line graph showing the amounts of interferon-$\gamma$(IFN-$\gamma$)) ("Secretion of IFN-$\gamma$ (pg/ml)"), measured by ELISA, in various dilutions of supernatants from cultures of cells of the CTL clone OT-1 (specific for the H-2 Kb/OVA257 molecular complex) either alone ("T cells alone") or with dendritic cells (DC) that had been pulsed with either medium alone ("T cell+DC (no peptide)"), the TA HIVtat-$OVA_{257}$ ("OT-1+DC+TA-$Ova_{257}$"), or the $OVA_{257}$ peptide epitope ("T cells+DC+$Ova_{257}$").

DC were pulsed with either the TA HIVtat-OVA$_{257}$ (see Table 2) or the peptide epitope OVA$_{257}$, each at a concentration of 10 μM, for 2 hours at 37° C. The cells were then washed free of the TA or peptide epitope and incubated for a further 48 hours. They were then cultured with cells of the OT-1 CTL clone (specific for H-2K$^b$/OVA$_{257}$) at a CTL to DC ratio of 10:1 for 24 hours. Supernatants were then removed from the cultures and the relative amounts of IFN-γ in various dilutions of each supernatant were measured by ELISA (FIG. 14). While insignificant levels of IFN-γ were produced by CTL cultured alone, CTL cultured with unpulsed DC, or CTL cultured with DC pulsed with OVA$_{257}$, a high level of IFN-γ was produced by CTL cultured with DC pulsed with HIVtat-OVA$_{257}$. These findings indicate that a peptide epitope persists in DC for a longer period of time when taken up by DC in the form of a TA than when taken up by DC in the form of the peptide epitope per se.

A number of embodiments of the invention have been described. Nevertheless, it will be understood that various modifications may be made without departing from the spirit and scope of the invention.

What is claimed is:

1. A fusion agent comprising:
   (a) an HIV tat transport domain;
   (b) at least two proteotlytic cleavage sites cleaved by the furin family of enzymes;
   (c) a first peptide epitope recognized by an antigen specific receptor on an effector CD4$^+$T lymphocyte wherein the first peptide epitope is between 9 and 30 amino acids in length; and
   (d) at least one additional peptide epitope recognized by an antigen specific receptor on an effector CD8$^+$T lymphocyte wherein the at least one additional epitope is between 8 and 12 amino acids in length;
   wherein there is a cleavage site between each of the peptide epitopes and between the peptide epitopes and the HIV tat transport domain in the fusion agent.

2. The fusion agent of claim 1 wherein the first peptide epitope can bind to a major histocompatability (MHC) class II molecule.

3. The fusion agent of claim 1 wherein the at least one additional peptide epitope can bind to a major histocompatability (MHC) class I molecule.

4. The fusion agent of claim 1 wherein the HIV tat transport domain is the HIV tat transport domain of SEQ ID NO: 1.

5. The fusion agent of claim 1 comprising at least two additional peptide epitopes recognized by an antigen specific receptor on an CD8$^+$T lymphocyte.

6. The fusion agent of claim 1, wherein the peptide epitode recognized by an antigen specific receptor on an CD4$^+$T lymphocyte is a MAGE epitope.

7. The fusion agent of claim 6, comprising two additional epitopes recognized by antigen specific receptors on effector CD8$^+$T lymphocytes, wherein the two additional epitopes are MAGE epitopes.

* * * * *